(12) United States Patent
Raslambekov

(10) Patent No.: US 11,517,400 B1
(45) Date of Patent: Dec. 6, 2022

(54) SYSTEMS AND METHODS FOR DETERMINING A POSITION FOR AN ORTHODONTIC ATTACHMENT

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

(21) Appl. No.: 17/720,409

(22) Filed: Apr. 14, 2022

(51) Int. Cl.
  *A61C 7/00* (2006.01)
  *G16H 20/40* (2018.01)

(52) U.S. Cl.
  CPC ............. *A61C 7/002* (2013.01); *G16H 20/40* (2018.01); *A61C 2007/004* (2013.01)

(58) Field of Classification Search
  CPC ... A61C 7/002; A61C 2007/004; G16H 20/40
  See application file for complete search history.

(56) References Cited

U.S. PATENT DOCUMENTS

| 5,011,405 | A | 4/1991 | Lemchen | |
| 6,413,084 | B1 * | 7/2002 | Rubbert | A61C 9/006 433/29 |
| 6,532,299 | B1 * | 3/2003 | Sachdeva | B33Y 80/00 382/128 |
| 6,905,337 | B1 | 6/2005 | Sachdeva | |
| 7,210,929 | B2 | 5/2007 | Raby et al. | |
| 7,296,996 | B2 | 11/2007 | Sachdeva et al. | |
| 7,347,686 | B2 | 3/2008 | Marshall | |
| 7,690,917 | B2 | 4/2010 | Marshall | |
| 7,837,464 | B2 | 11/2010 | Marshall | |
| 8,194,067 | B2 | 6/2012 | Raby et al. | |
| 8,562,339 | B2 | 10/2013 | Raby et al. | |
| 9,326,831 | B2 | 5/2016 | Cheang | |
| 9,503,282 | B2 | 11/2016 | Kody et al. | |
| 10,136,964 | B2 | 11/2018 | Borovinskih et al. | |
| 10,517,482 | B2 | 12/2019 | Sato et al. | |
| 10,631,956 | B1 | 4/2020 | Raslambekov | |
| 10,726,949 | B1 | 7/2020 | Raslambekov et al. | |
| 10,751,149 | B1 * | 8/2020 | Raslambekov | G06T 7/0012 |
| 10,758,323 | B2 | 9/2020 | Kopelman | |
| 10,856,954 | B1 | 12/2020 | Raslambekov | |
| 10,950,061 | B1 | 3/2021 | Raslambekov | |
| 10,993,782 | B1 | 5/2021 | Raslambekov | |
| 11,058,515 | B1 | 7/2021 | Raslambekov | |

(Continued)

*Primary Examiner* — Nicholas D Lucchesi
(74) *Attorney, Agent, or Firm* — BCF LLP

(57) ABSTRACT

A method and a system for determining an orthodontic treatment plan including a tooth stripping step are provided. The method comprises: acquiring a 3D digital model of a first tooth and a second tooth of the subject, the second tooth being adjacent the first tooth; receiving a stripping request for stripping tooth material, from at least one of the first tooth along a first stripping plane and the second tooth along a second stripping plane; determining, along a surface of the first tooth, a first area of interest; determining, along the surface of the second tooth, a second area of interest; determining a distance between a first set of vertices associated with the first area of interest and a second set of vertices associated with the second area of interest; in response to the distance being greater than a predetermined distance threshold, denying, by the processor, the stripping request.

20 Claims, 13 Drawing Sheets

(56) References Cited

U.S. PATENT DOCUMENTS

| | | |
|---|---|---|
| 11,103,330 B2 | 8/2021 | Webber et al. |
| 11,166,787 B1 | 11/2021 | Raslambekov |
| 11,191,618 B1 | 12/2021 | Raslambekov |
| 11,348,257 B2* | 5/2022 | Lang ................ A61B 34/25 |
| 2007/0099146 A1 | 5/2007 | Reising |
| 2013/0325431 A1* | 12/2013 | See .................. A61C 7/002 |
| | | 703/11 |
| 2015/0019176 A1* | 1/2015 | Presswood ........... G06F 30/00 |
| | | 703/1 |
| 2017/0165032 A1 | 6/2017 | Webber et al. |
| 2017/0231721 A1 | 8/2017 | Akeel et al. |
| 2018/0174367 A1* | 6/2018 | Marom ............... G06F 3/011 |
| 2018/0325626 A1 | 11/2018 | Huang |
| 2019/0015177 A1* | 1/2019 | Elazar ................ G16H 30/40 |
| 2019/0125493 A1* | 5/2019 | Salah ................. G16H 50/70 |
| 2019/0298494 A1 | 10/2019 | Webber et al. |
| 2020/0188062 A1 | 6/2020 | Kopelman et al. |
| 2021/0106403 A1* | 4/2021 | Aptekarev ........... G16H 20/30 |
| 2021/0196430 A1* | 7/2021 | Wilson ............... A61B 5/0088 |
| 2021/0251723 A1* | 8/2021 | Raslambekov ....... G06T 7/0012 |

\* cited by examiner

SYSTEMS AND METHODS FOR DETERMINING A POSITION FOR AN ORTHODONTIC ATTACHMENT

FIELD

The present technology relates generally to systems and methods for determining an orthodontic treatment for a subject; and in particular, to methods and systems for determining a position for an orthodontic attachment on a tooth surface.

BACKGROUND

A typical orthodontic treatment includes a number of consecutive treatment steps in which orthodontic appliances are consecutively used to apply forces to a subject's teeth to move the subject's teeth from a respective start position to a desired position, typically associated with alignment of the subject's teeth or normal occlusion thereof. For example, such orthodontic appliances can include brackets, braces, elastics or orthodontic aligners.

In one example, the orthodontic appliance comprises an orthodontic elastic. The orthodontic elastic can be attached to lower teeth on a lower jaw and upper teeth on an upper jaw of the subject causing, through applying thereto a certain amount of elastic force, a desired position of the lower jaw relative to the upper jaw of the subject.

Typically, such elastics are applied to the subject's teeth via specific orthodontic attachments attached to predetermined lower and upper teeth of the subject.

However, efficacy of using the orthodontic elastics depends on positions of the orthodontic attachments on surfaces of the predetermined teeth of the subject. Another consideration is wear comfort to the subject, particularly when the subject must also wear an aligner in addition to the elastic.

Certain prior art approaches have been developed to address the technical problem of determining an optimal position for such orthodontic attachments.

U.S. Pat. No. 11,166,787-B1, issued on Nov. 9, 2021, assigned to Arkimos Ltd., and entitled "ORTHODONTIC ATTACHMENT SYSTEMS AND METHODS" discloses systems and methods for determining a coupling point for an attachment on a tooth of a subject comprising: obtaining a digital 3D representation of the tooth to which the attachment will be coupled; obtaining attachment data indicative of the attachment to be coupled to the tooth; determining, on the digital 3D representation of the tooth, a plurality of excluded areas for the coupling point based on the digital 3D representation of the tooth and the attachment data; determining the coupling point by identifying an area on the tooth which is not in the plurality of excluded areas; and storing, in a memory of the computer system, the determined coupling point.

U.S. Pat. No. 9,326,831-B2, issued on May 3, 2016, assigned to Align Technology Inc, and entitled "SYSTEM AND METHOD FOR POSITIONING THREE-DIMENSIONAL BRACKETS ON TEETH", discloses systems and methods for positioning 3D virtual brackets on teeth for the precise positioning of conventional brackets and wire. Various reference features may be calculated for the teeth and used to calculate a position for the virtual bracket. Reference features that are calculated include curve of Spee, Andrew's plane, and a facial axis of the clinical crown for the teeth.

U.S. Pat. No. 9,503,282-B2, issued on Nov. 22, 2016, assigned to 3M Innovative Properties Co, and entitled "METHODS AND SYSTEMS FOR DETERMINING THE POSITIONS OF ORTHODONTIC APPLIANCES", discloses determining positions of orthodontic appliances such as brackets and buccal tubes on a patient's teeth using digital data that represents the shapes of the patient's teeth. Certain landmarks of the teeth such as the marginal ridges are determined using software, and the software adjusts positions of the virtual appliances on the teeth as needed in order to bring the marginal ridges into proper alignment at the conclusion of treatment. The resulting positions are optionally used to determine the location of the appliances in an indirect bonding apparatus such as a transfer tray.

U.S. Pat. No. 10,136,964-B2, issued on Nov. 27, 2018, assigned to Align Technology Inc, and entitled "AUTOMATIC PLACEMENT OF PRECISION CUTS", discloses an orthodontic positioning device and methods for making an orthodontic positioning device including a first patient removable orthodontic tooth positioning appliance having teeth receiving cavities shaped to receive and apply a resilient positioning force to a patient's teeth provided in one of an upper jaw and a lower jaw. The first appliance includes a hook configured to receive an orthodontic elastic band. The orthodontic positioning device also includes a second patient removable orthodontic tooth positioning appliance having teeth receiving cavities shaped to receive and apply a resilient positioning force to a patient's teeth provided in the other of the upper jaw and the lower jaw. The second appliance includes a cutout operable to expose an orthodontic elastic band receiving member.

SUMMARY

Developers of the present technology have appreciated that a more optimal position for a given orthodontic attachment, such as for attaching an elastic thereto, can be determined based on reference points specifically determined on the surface of the given tooth.

More specifically, at least some non-limiting embodiments of the present technology are directed to methods and systems for determining, on one of a lingual surface and a buccal surface of the given tooth, a work area based on curvature of a side surface of the given tooth. Further, the present methods and system are directed to determining, within the work area, a reference point as being a point that is most distant from all points defining a contour of the work area. This reference point can further be used as a boundary within the surface of the given tooth of a positioning space for the given orthodontic attachment.

Thus, the positioning space so determined based at least on this reference point is believed to provide a more accurate positioning of the given orthodontic attachment on the surface of the given tooth which would allow for a more accurate application of the additional force applied by the elastic, to the subject's teeth. In embodiments when the subject is also wearing an aligner over the teeth, improved wear comfort can be achieved based on the determined configuration of the positioning orthodontic attachment.

By doing so, an increased overall efficacy of the orthodontic treatment can be attained.

More specifically, in accordance with a first broad aspect of the present technology, there is provided a method of determining a position of an orthodontic attachment on a surface of a given tooth of a subject. The method is executable by a processor. The method comprises: acquiring, by the processor, a 3D digital model of a subject's arch form, the 3D digital model including a plurality of vertices representing a surface of the given tooth of the subject; determining, by the processor, along the surface of the given tooth, a work area for positioning thereon the orthodontic attachment, the work area having a contour defined by contour vertices of the plurality of vertices; determining, by the processor, a reference vertex of the work area by determining a vertex of the plurality of vertices within the work area which is most distant from all of the contour vertices, the reference vertex being representative of a boundary of a space within the work area for positioning therein the orthodontic attachment; and storing, by the processor, data of the reference vertex of the work area for further use in determining the position of the orthodontic attachment on the surface of the given tooth.

In some implementations of the method, the plurality of vertices of the 3D digital model of the subject's arch form further includes vertices representing surfaces of a plurality of subject's teeth, including the given tooth, and wherein: the determining the contour of the work area comprises: obtaining, by the processor, a jaw curve extending through each one of the plurality of subject's teeth along the subject's arch form; determining, by the processor, a reference plane extending through the given tooth, in a buccolabial direction thereof, perpendicularly to the jaw curve; for a given vertex representative of the surface of the given tooth, determining, by the processor, a respective angular difference between a normal vector to the surface at the given vertex and the reference plane; in response to the respective angular difference being greater than a predetermined angular threshold value, removing, by the processor, the given vertex from further consideration; and in response to the respective angular difference being lower than or equal to the predetermined angular threshold value, determining, by the processor, the given vertex as being representative of the work area of the surface of the given tooth for positioning there on the orthodontic attachment.

In some implementations of the method, the method further comprises determining the jaw curve as a curve extending through respective centers of each one the plurality of subject's teeth.

In some implementations of the method, the determining the vertex of the plurality of vertices within the work area which is most distant from all of the contour vertices comprises determining a vertex from which a summation of distance values to each one of the contour vertices is maximum.

In some implementations of the method, the determining the vertex from which the summation of the distance values to each one of the contour vertices is maximum comprises applying a Dijkstra algorithm.

In some implementations of the method, the method further comprises determining, by the processor, the reference vertex of the work area as corresponding to a vertical boundary of the space within the work area, towards a crown of the given tooth, for positioning thereon the orthodontic attachment.

In some implementations of the method, the method further comprises: retrieving, from a memory communicatively coupled with the processor, a respective pattern representative of a shape of the space within the work area associated with the given tooth for positioning thereon the orthodontic attachment; fitting the respective pattern within the work area such that at least one first peak point of the respective pattern positioned towards the crown of the given tooth matches the reference vertex of the work area; and adding, by the processor, to the 3D digital model of the subject's arch form, an indication of the respective pattern fitted within the work area associated with the given tooth for further use in producing the orthodontic appliance.

In some implementations of the method, the plurality of vertices of the 3D digital model further includes vertices representing a gingiva of the subject, and the method further comprises: obtaining, by the processor, a segmentation contour representative of a boundary between the given tooth and the gingiva; identifying, on the segmentation contour along the work area, based on a predetermined rule, additional reference vertices for positioning the orthodontic attachment; and wherein: the fitting further comprises fitting the respective pattern within the work area such that at least one second peak point of the respective pattern, oppositely facing the at least one first peak point, matches a respective one of the additional reference vertices.

In some implementations of the method, the additional reference vertices are distributed uniformly along the segmentation contour.

In some implementations of the method, the method further comprises determining the segmentation contour.

In some implementations of the method, the fitting comprises scaling the respective pattern within the work area in at least one direction thereof.

In some implementations of the method, the orthodontic attachment is to be applied to the given tooth concurrently with an orthodontic appliance; and a contour of the space within the work area associated with the given tooth defines a cut-out in the orthodontic appliance for accommodating therein the orthodontic attachment when applied to the subject's arch form.

In some implementations of the method, the method further comprises determining, based at least on a configuration of the cut-out, a profile of a free end of the orthodontic appliance configured for accommodating therein the orthodontic attachment.

In some implementations of the method, the method further comprises causing manufacture of the orthodontic appliance based at least on the determined profile of the free end thereof.

In some implementations of the method, the orthodontic attachment is an elastic retaining member.

In some implementations of the method, the orthodontic appliance is an orthodontic aligner.

In accordance with a second broad aspect of the present technology, there is provided a system for determining a position of an orthodontic attachment on a surface of a given tooth of a subject. The system comprises: a processor and a non-transitory computer-readable memory storing instructions. The processor, upon executing the instructions, is configured to: acquire a 3D digital model of a subject's arch form, the 3D digital model including a plurality of vertices representing a surface, at least, of the given tooth of the subject; determine, along the surface of the given tooth, a work area for positioning thereon the orthodontic attachment, the work area having a contour defined by contour vertices of the plurality of vertices, the reference vertex being representative of a boundary of a space within the work area for positioning therein the orthodontic attachment; and determine a reference vertex of the work area by determining a vertex of the plurality of vertices within the work area which is most distant from all of the contour vertices; and store data of the reference vertex of the work area for further use in positioning the orthodontic attachment on the surface of the given tooth.

In some implementations of the system, the plurality of vertices of the 3D digital model of the subject's arch form further includes vertices representing surfaces of a plurality of subject's teeth, including the given tooth, and wherein to determine the contour of the work area, the processor is further configured to: obtain a jaw curve extending through each one of the plurality of subject's teeth along the subject's arch form; determine a reference plane extending through the given tooth, in a buccolabial direction thereof, perpendicularly to the jaw curve; for a given vertex representative of the surface of the given tooth, determine a respective angular difference between a normal vector to the surface at the given vertex and the reference plane; in response to the respective angular difference being greater than a predetermined angular threshold value, remove the given vertex from further consideration; and in response to the respective angular difference being lower than or equal to the predetermined angular threshold value, determine the given vertex as being representative of the work area of the surface of the given tooth for positioning there on the orthodontic attachment.

In some implementations of the system, to determine the vertex of the plurality of vertices within the work area which is most distant from all of the contour vertices, the processor is configured to determine a vertex from which a summation of distance values to each one of the contour vertices is maximum.

In some implementations of the system, the processor is further configured to: determine the reference vertex of the work area as corresponding to a vertical boundary of a space within the work area, towards a crown of the given tooth, for positioning thereon the orthodontic attachment; retrieve, from the non-transitory computer-readable memory, a respective pattern representative of a shape of the space within the work area associated with the given tooth for positioning thereon the orthodontic attachment; fir the respective pattern within the work area such that at least one first peak point of the respective pattern positioned towards the crown of the given tooth matches the reference vertex of the work area; and add, to the 3D digital model of the subject's arch form, an indication of the respective pattern fitted within the work area associated with the given tooth for further use in producing the orthodontic appliance.

In the context of the present specification, unless expressly provided otherwise, the term "orthodontic treatment" is broadly referred to as any type of medical intervention aimed at correcting malocclusions associated with the teeth or jaw of the subject, or moving the subject's teeth or jaws for any reason, including surgical and non-surgical manipulations, such as, but not limited to, using one or more of aligners, brackets, multi-strand wires, strips, retainers, and plates. Further, the orthodontic treatment, as referred to herein, may be determined automatically by a software, based on image data and other inputs associated with the subject, or semi-automatically with input from a practitioner in the field of dentistry (such as an orthodontist, a maxillofacial surgeon, for example).

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid-state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

It should be noted that, unless otherwise explicitly specified herein, the drawings are not to scale.

DETAILED DESCRIPTION

Certain aspects and embodiments of the present technology are directed to methods of and systems for determining a position for an orthodontic attachment (such as an orthodontic attachment configured to retain an orthodontic elastic, for example), and based on the determined position, determining a shape for an orthodontic appliance, such as braces or an aligner, which can be applied to subject's teeth concurrently with the orthodontic attachment.

More specifically, certain aspects and embodiments of the present technology comprise a computer-implemented method of determining, based on a 3D digital model of a subject's arch form, including a given tooth, a work area on a surface of the given tooth where the orthodontic attachment can be positioned. Further, the present methods are directed to determining a specific reference point within the work area, which is used in positioning the orthodontic attachment on the surface of the given tooth. For example, for orthodontic attachments which have a base portion and a distal end portion with a protrusion to which the elastic can be attached, the determined reference point can correspond to a position of the protrusion when projected onto the surface of the given tooth.

Certain embodiments of the present technology minimize, reduce or avoid some of the problems noted with the prior art. For example, implementing certain embodiments of the present technology, may allow increasing effectiveness of the orthodontic treatment including application of the above-mentioned orthodontic appliances.

For example, the increased effectiveness of the orthodontic treatment can be achieved by determining such a position for the orthodontic attachment on the surface of the given tooth such that an actual value of an additional force to be exerted on the at least one of the subject's teeth by the orthodontic elastic would more precisely correspond to a predetermined value of the additional force required to attain the normal occlusion between the upper and lower teeth of the subject.

In another example, the increased effectiveness of the orthodontic treatment can also be achieved by determining the position for the orthodontic attachment on the surface of the given tooth in such a way that a concurrent application of the orthodontic appliance and the orthodontic attachment would allow for a better wear comfort thereof for the subject, which may thus increase subject's adherence to the orthodontic treatment.

Orthodontic Treatment

Figure 1:
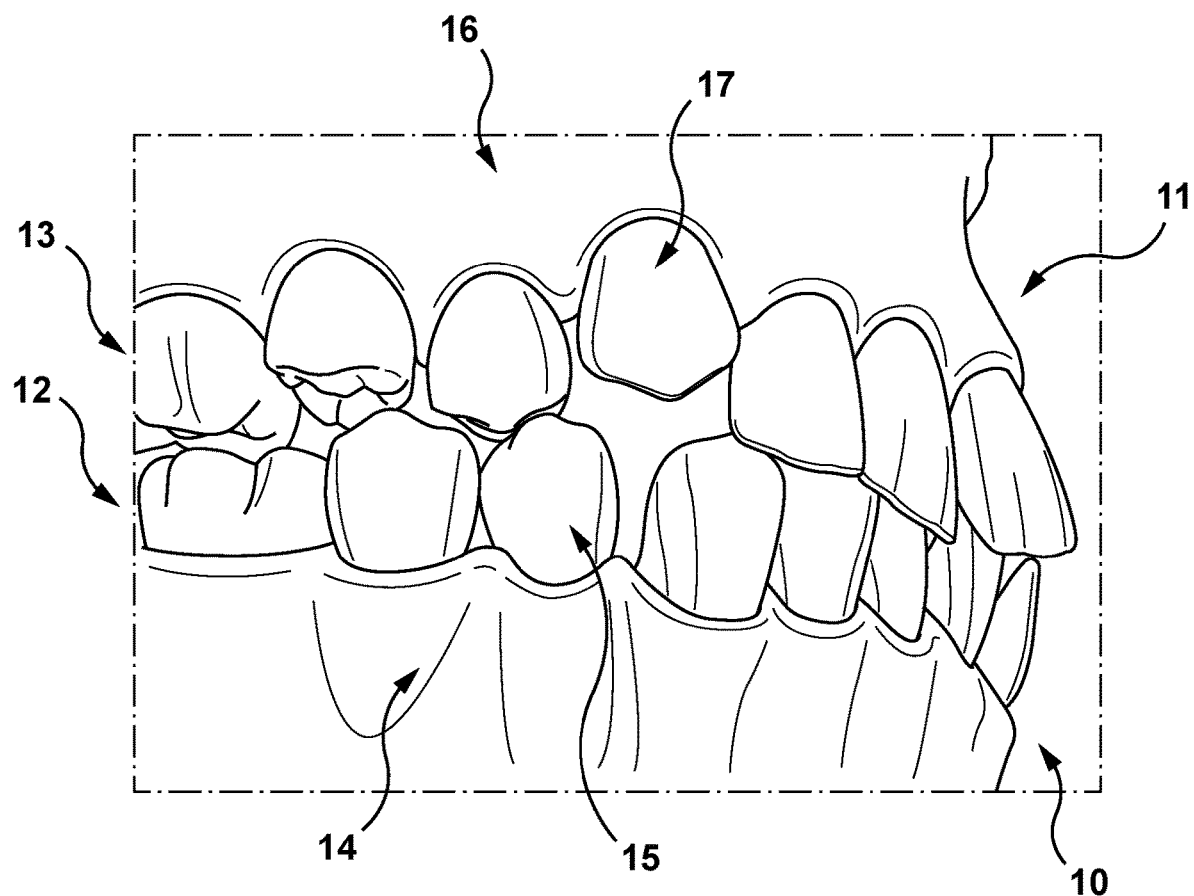
FIG. 1 depicts a perspective view of lower and upper arch forms of a subject depicting examples of malocclusions of some of subject's teeth, in accordance with certain non-limiting embodiments of the present technology.

With initial reference to FIG. 1, there is depicted a perspective view of a lower arch form 10 and an upper arch form 11 of the subject (not depicted), to which certain aspects and non-limiting embodiments of the present technology may be applied.

As it can be appreciated, the lower arch form 10 includes lower teeth 12 and a lower gingiva 14; and the upper arch form 11 includes upper teeth 13 and upper gingiva 16. Further, in the depicted embodiments of FIG. 1, positions of at least some of the lower teeth 12 within the lower arch form 10 and those of the upper teeth 13 within the upper arch form 11 may be indicative of certain orthodontic disorders of the subject. For example, at least a given lower tooth 15 and a given upper tooth 17 are misaligned within a respective one of the lower arch form 10 and the upper arch form 11. Further, as the given lower tooth 15 is abnormally embedded within the lower teeth 12 while the given upper tooth 13 abnormally protrudes over opposing ones of the lower teeth 12, the misalignment thereof may affect the bite of the teeth, or, in other words, cause a malocclusion—that is, an irregular spatial relationship—between the lower teeth 12 and the upper teeth 13.

Other malocclusions (not depicted) associated with misalignment of lower teeth 12 relative to each other and the upper teeth 13, according to certain non-limiting embodiments of the present technology, may include, without limitation: overbites, underbites, crossbites, openbites, crowding of some of the lower teeth 12 and the upper teeth 13, midline shift therebetween, and others.

In some non-limiting embodiments of the present technology, for resolving the above-mentioned malocclusions, an orthodontic treatment may be provided to the subject.

In some non-limiting embodiments of the present technology, the orthodontic treatment may comprise applying an orthodontic appliance to the teeth of the subject. Generally speaking, the orthodontic appliance may be configured to exert a respective predetermined force onto at least some of the lower teeth 12 and the upper teeth 13—such as the given lower tooth 15 and the given upper tooth 17, causing them to move towards an aligned position, thereby restoring the normal occlusion of the lower teeth 12 relative to upper teeth 13 of the subject. More specifically, in the depicted embodiments of FIG. 1, the orthodontic appliance may be configured to cause the given lower tooth 15 to move outwardly between lower teeth adjacent thereto; and further cause clockwise rotation thereof. Further, the orthodontic appliance may be configured to cause the given upper tooth 17 to move inwardly. In various non-limiting embodiments of the present technology, the orthodontic appliance may comprise orthodontic appliances of different types, shapes, sizes and configurations, such as those including, without limitation, aligners, brackets, multi-strand wires, strips, retainers, and plates.

In some non-limiting embodiments of the present technology, the orthodontic appliance may be selected, in the course of the orthodontic treatment to correct a respective malocclusion. For example, in some non-limiting embodiments of the present technology, the orthodontic appliance may include a bracket system including: (i) brackets to be attached to at least some of the lower teeth 12 and/or the upper teeth 13; and (ii) a wire typically produced from a shape memory alloy, such as Nitinol™, as an example, that is received in the brackets of the lower teeth 12 or the upper teeth 13.

Figure 2A:
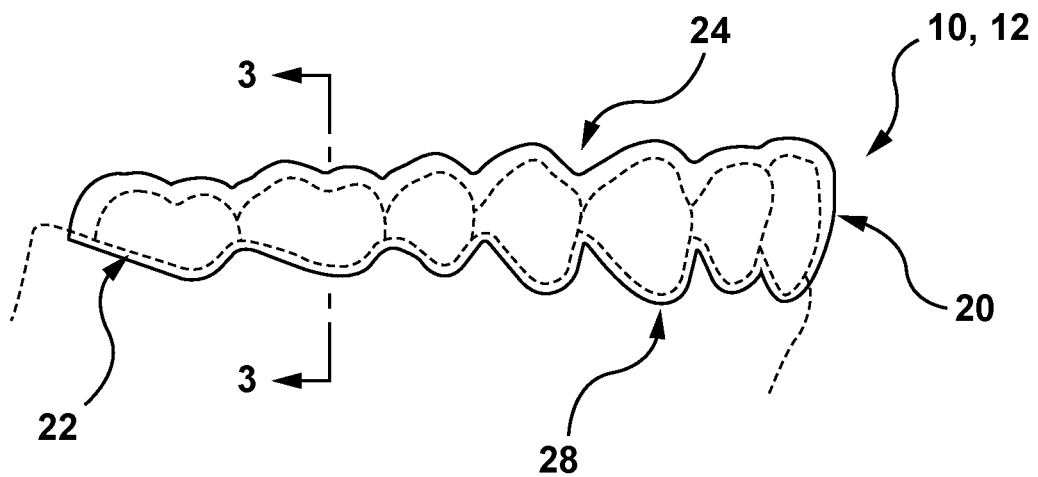
FIGS. 2A and 2B depict a side view and a cross-sectional view through line 3-3, respectively, of an orthodontic appliance applied to the subject's teeth that may be configured to treat the malocclusions of the subject's teeth present in FIG. 1, in accordance with certain non-limiting embodiments of the present technology.
Figure 2B:
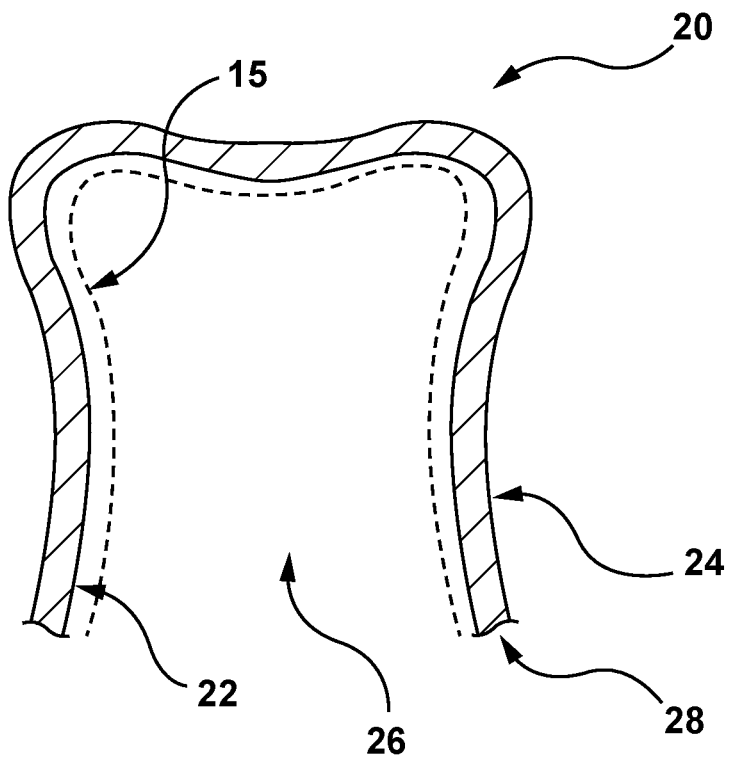

In specific non-limiting embodiments of the present the present technology, the orthodontic appliance may include at least one aligner. With reference to FIGS. 2A and 2B, there is depicted an aligner 20 applied to at least some of the lower teeth 12, in accordance with certain non-limiting embodiments of the present technology. The aligner 20 comprises an inner surface 22 and an outer surface 24. The inner surface 22 defines a channel 26, which is configured, in some non-limiting embodiments of the present technology, for receiving crown portions of at least some of the lower teeth 12, such as the given lower tooth 15. However, in other non-limiting embodiments of the present technology, the channel 26 of the aligner 20 may be configured to receive crown portions of all of the lower teeth 12. At least one edge, such as a front edge 28 (also referred to herein as an "open edge"), of the channel 26 is shaped for following a gum line (not separately numbered) along the lower gingiva 14.

It will be appreciated that, in accordance with certain non-limiting embodiments of the present technology, the aligner 20 may be used for treating different teeth malocclusions, including but not limited to one or more of: closing interdental spaces ("space closure"), creating/widening interdental spaces, tooth rotation, tooth intrusion/extrusion, and tooth translation, to name a few. It should further be noted that in certain non-limiting embodiments of the present technology, applying the aligner 20 to the lower teeth 12 may further include applying specific attachments thereto.

As may become apparent, the aligner 20 may be designed in such a way that its inner surface 22 is configured to impose respective forces on one or more of the lower teeth 12 to obtain a desired position of the lower teeth 12 at a given stage of the orthodontic treatment.

Needless to say that, although in the depicted embodiments of FIGS. 2A and 2B, the aligner 20 is configured to be applied onto the lower teeth 12, in other non-limiting embodiments of the present technology, a respective configuration of the aligner 20 may be applied to the upper teeth 13 of the subject for treating misalignment of at least some thereof—such as the given upper tooth 17. By so doing, the desired occlusion between the lower teeth 12 and the upper teeth 13 may be attained.

According to certain non-limiting embodiments of the present technology, the aligner 20 may be made of a polymer, such as a thermoplastic material. In other non-limiting embodiments of the present technology, the aligner 20 may be made of poly-vinyl chloride (PVC). In yet other non-limiting embodiments of the present technology, the aligner 20 may be made of polyethylene terephthalate glycol (PETG). Other suitable materials can also be used to form the aligner 20.

In some non-limiting embodiments of the present technology, the aligner 20 may be manufactured using additive manufacturing techniques, such as 3D printing techniques where the aligner 20 is formed by printing according to a pre-generated 3D representation thereof.

In other non-limiting embodiments of the present technology, the aligner 20 may be produced by a thermoforming process where (1) an unfinished aligner is produced, using a preform, on a respective aligner mold (not depicted) associated with a respective stage of the orthodontic treatment, which is configured to shape the inner surface 22 of the aligner 20; and (2) the unfinished aligner is cut along a predetermined cut line to remove excess material therefrom, thereby producing the aligner 20, the predetermined cut line defining the at least one edge of the channel 26 of the aligner 20, such as that of the front edge 28.

In specific non-limiting embodiments of the present technology, the aligner 20 may be manufactured in accordance with one or more methods described in a co-owned U.S. Pat. No. 11,191,618-B1, issued on Dec. 7, 2021, and entitled "SYSTEMS AND METHODS FOR FORMING A DENTAL APPLIANCE,", the content of which is incorporated herein by reference in its entirety.

Also, in certain cases, to attain a desired relative position between the lower and upper arch forms 10, 11 and hence the lower teeth 12 and upper teeth 13, it may be advantageous to use an other orthodontic appliance (also referred to herein as an "auxiliary orthodontic appliance") to a surface of at least one of the subject's teeth, such as the given lower tooth 15. In some non-limiting embodiments of the present technology, the other orthodontic appliance can comprise an orthodontic elastic, made of elastic material, such as rubber, latex, and the like, configured to be attached to an orthodontic attachment on the lower teeth 12 and another orthodontic attachment on the upper teeth 13, the orthodontic elastic being stretched between the upper and the lower tooth for re-positioning a relative position between the lower teeth 12 and the upper teeth 13.

Figure 3A:
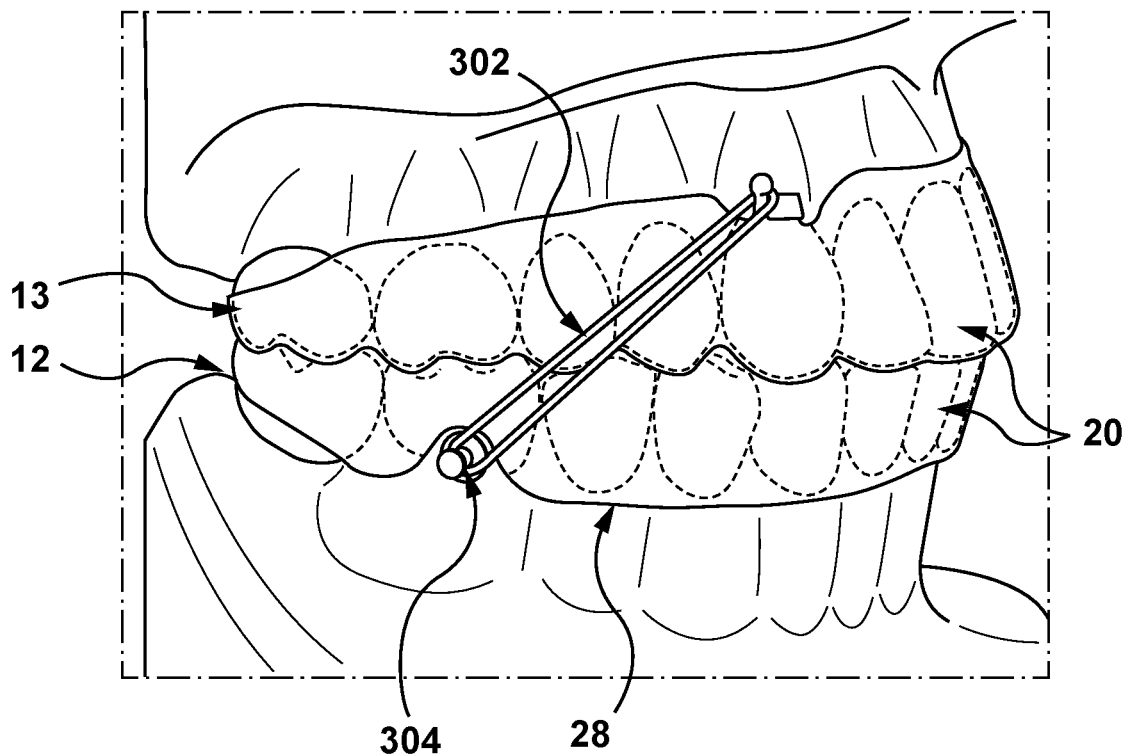
FIG. 3A depicts a schematic diagram of an auxiliary orthodontic appliance applied to the subject's teeth concurrently with the orthodontic appliance of FIGS. 2A and 2B, in accordance with certain embodiments of the present technology.
Figure 3B:
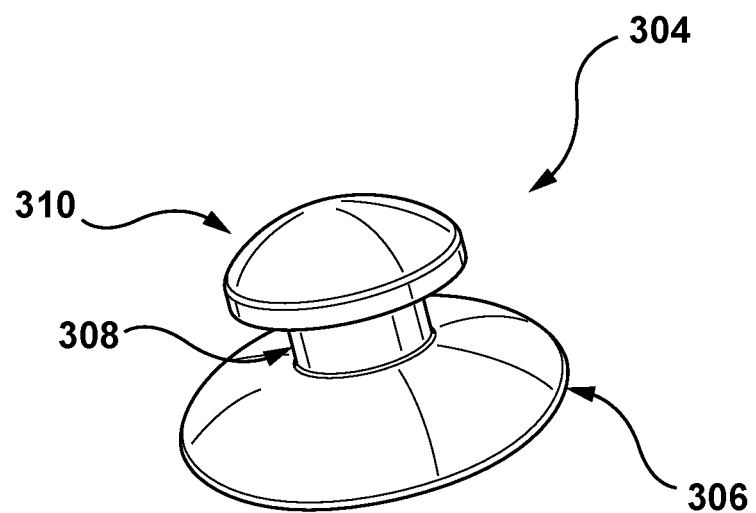
FIG. 3B depicts a schematic diagram of an orthodontic attachment used for retaining the auxiliary orthodontic appliance of FIG. 3A on the subject's teeth, in accordance with certain non-limiting embodiments of the present technology.

With reference to FIGS. 3A and 3B, there is depicted a schematic diagram illustrating an orthodontic elastic 302 extending between the lower teeth 12 and the upper teeth 13, in addition to the aligner 20, in accordance with certain non-limiting embodiments of the present technology.

As it can be appreciated from FIG. 3A, according to certain non-limiting embodiments of the present technology, the orthodontic elastic 302 can comprise a band which is looped around orthodontic attachments attached to respective ones of the lower teeth 12 and the upper teeth 13, such as an orthodontic attachment 304 attached to the given lower tooth 15, as an example.

To the upper teeth 13, in one example, the orthodontic elastic 302 can be attached via an attachment similar to the orthodontic attachment 304 (not depicted in FIG. 3A). However, in another example depicted in FIG. 3A, the orthodontic elastic 302 can be attached to the upper teeth 13 via a specific hook defined within a body of the aligner 20. An elasticity value of the material of the orthodontic elastic 302 and a size thereof (such as a diameter) define a force to be applied to the lower and upper teeth 12, 13, which can thus be selected such that the lower teeth 12 and the upper teeth 13, while at rest, are retained in a desired occlusion (such that corresponding to the normal occlusion therebetween, for example).

Further, it is not limited how the orthodontic attachment 304 can be implemented. In a specific non-limiting example depicted in FIG. 3B, the orthodontic attachment 304 can include at least (i) a base portion 306 configured for attaching to the surface of the given lower tooth 15; (ii) a neck portion 308, around which the orthodontic elastic 302 can be looped; and (iii) a head portion 310 configured for retaining the orthodontic elastic 302 on the neck portion 308. For example, the orthodontic attachment 304 can be produced from a metal, such as a stainless-steel alloy.

It should be noted that in various non-limiting embodiments of the present technology, depending on a particular application, the orthodontic attachment 304 can have different configurations including, without limitation, a different form factor of at least one of the base portion 306, the neck portion 308, and the head portion 310; a different material thereof; different dimensions thereof, and the like. For example, in specific non-limiting embodiments of the present technology, instead of having the neck portion 308 and the head portion 310, to retain the orthodontic elastic 302, the orthodontic attachment 304 can include a hook attached to the base portion 306.

Further, as it can also be appreciated from FIG. 3A, to accommodate the orthodontic attachment 304 on the surface of the given lower tooth 15, the front edge 28 of the aligner 20 may need to be modified to define a respective cut-out therein allowing for concurrent application of both the aligner 20 and the orthodontic attachment 304 to the given lower tooth 15.

However, a coupling location of the base portion 306 of the orthodontic attachment 304 to the surface of the given lower tooth 15 should be carefully determined as it may affect the actual value of the force to be applied to the lower and upper teeth 12, 13 by the orthodontic elastic 302 lowering an overall efficacy of the orthodontic treatment. For example, failing to determine a correct coupling position for the orthodontic attachment 304 may further result in the orthodontic elastic 302 connected thereto imposing an insufficient amount of the elastic force to the lower teeth 12. In another example, an uncarefully selected coupling position for the orthodontic attachment 304 can cause the orthodontic elastic 302 to impose a greater amount of the elastic force to the lower teeth 12, which can cause damage to the lower arch form 10 or even to an entire lower jaw of the subject (not separately numbered), such as damage to at least one mandibular head thereof; or an additional misalignment between the lower teeth 12 and the upper teeth 13.

In yet another example, notwithstanding the above, the selected coupling position for the orthodontic attachment 304 can cause wear discomfort to the subject. This in turn can affect subject's adherence to the orthodontic treatment, which may thus result in lowered efficacy thereof.

Thus, the developers of the present technology have devised methods and systems for determining an optimal coupling position for the orthodontic attachment 304. More specifically, the present methods and systems are directed to determining the coupling position of the orthodontic attachment 304 within a work area (such as a work area 910 depicted in FIG. 9B) specifically determined on the surface of the given lower tooth 15, using, for example a 3D digital model thereof.

Further, according to certain non-limiting embodiments of the present technology, the present methods are directed to obtaining an indication of a respective pattern (such as a given pattern 1104 depicted in FIG. 11), corresponding to a particular geometry of the base portion 306 of the orthodontic attachment 304, and thus representative of a shape of a positioning space (such as a positioning space 1210 depicted in FIG. 12B) within the work area 910 for positioning thereon the orthodontic attachment 304. Further, the methods include fitting the given pattern 1104 within the work area 910, which can include: (i) determining, within the work area 910, a reference vertex of the 3D digital model representative of a boundary of the positioning space towards the crown portion of the given lower tooth 15; and (ii) additional reference vertices representative of a boundary of the positioning space towards the lower gingiva 14. Further, the present methods are directed to fitting, such as by scaling, the given pattern 1104 between the so determined reference vertices on the 3D digital model of the given lower tooth 15, thereby determining the positioning space 1210 for the orthodontic attachment 304 on the surface thereof.

Further, considering the positioning space 1210 on the surface of the given lower tooth 15, a configuration of the respective cut-out on the body of the aligner 20 can be determined, defining an updated profile of the front edge 28 thereof. The updated profile of the front edge 28 can thus enable simultaneous use of the aligner 20 and the orthodontic attachment 304 on the lower teeth 12.

Therefore, the positioning space 1210 for the orthodontic attachment 304 can allow for a more optimal amount of the elastic force imposed by the orthodontic elastic 302 as well as for improved wear comfort of the aligner 20 thus produced based on data of the updated profile of the front edge 28 thereof. How the positioning space 1210 can be determined, in accordance with certain non-limiting embodiments of the present technology, will be described below with reference to FIGS. 6 to 13B.

System

Figure 4:
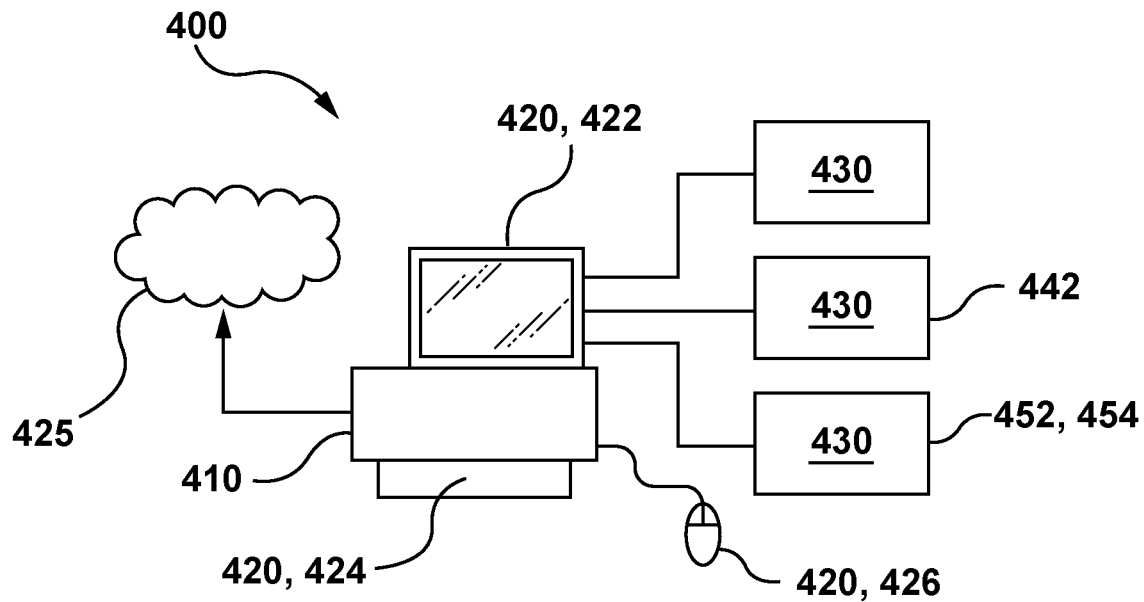
FIG. 4 depicts a schematic diagram of a computer system for determining a position of the orthodontic attachment of FIG. 3A on a surface of a given tooth of a subject, in accordance with certain non-limiting embodiments of the present technology.
Figure 5:
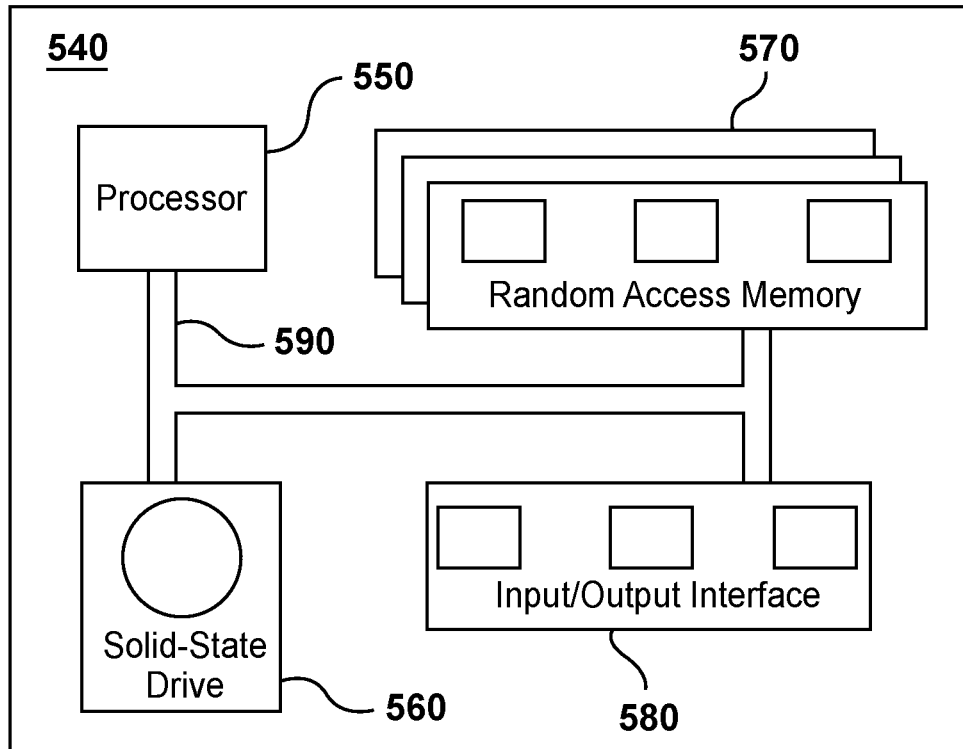
FIG. 5 depicts a schematic diagram of a computing environment, including a processor, of the system of FIG. 4, in accordance with certain embodiments of the present technology.

With reference to FIGS. 4 and 5, there is depicted a schematic diagram of a system 400 suitable for determining a position for an orthodontic attachment, such as the orthodontic attachment 304 mentioned above, in accordance with certain non-limiting embodiments of the present technology.

It is to be expressly understood that the system 400 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 400 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 400 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 400 of FIG. 4 comprises a computer system 410. The computer system 410 may be configured, by pre-stored program instructions, to determine, based on image data associated with the subject, such as the 3D digital model of the given lower tooth 15, the position for the orthodontic attachment 304 on the surface of the given lower tooth 15, and further using data of the position of the orthodontic attachment 304, determine a cut line defining a configuration of at least an edge of at least one wall of the channel 26, such as the front edge 28, of the aligner 20. In additional non-limiting embodiments of the present technology, the computer system 410 may further be configured to produce at least one configuration of the aligner 20 based on the so planned orthodontic treatment.

To that end, in some non-limiting embodiments of the present technology, the computer system 410 may be configured to receive image data pertaining to the subject or to a given stage of the orthodontic treatment. According to some non-limiting embodiments of the present technology, the computer system 410 may receive the image data via local input/output interface (such as USB, as an example, not separately depicted). In other non-limiting embodiments of the present technology, the computer system 410 may be configured to receive the image data over a communication network 425, to which the computer system 410 is communicatively coupled.

In some non-limiting embodiments of the present technology, the communication network 425 is the Internet and/or an Intranet. Multiple embodiments of the communication network may be envisioned and will become apparent to the person skilled in the art of the present technology. Further, how a communication link between the computer system 410 and the communication network 425 is implemented will depend, inter alia, on how the computer system 410 is implemented, and may include, but is not limited to, a wire-based communication link and a wireless communication link (such as a Wi-Fi communication network link, a 3G/4G communication network link, and the like).

It should be noted that the computer system 410 can be configured for receiving the image data from a vast range of devices. Some of such devices can be used for capturing and/or processing data pertaining to maxillofacial and/or cranial anatomy of the subject. In certain embodiments, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a tooth (such as a crown portion of the given lower tooth 15, not separately numbered) extending outwardly of the gingival sulcus. In some embodiments, the image data is indicative of properties of internal portions of the anatomical structures, for example, volumetric properties of bone surrounding an internal portion of the tooth (for example, a root portion of the given lower tooth 15, not depicted) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

Further, as noted above, after the determining the tooth trajectory for the given lower tooth 15, in some non-limiting embodiments of the present technology, the system 400 may be configured, based on a respective 3D digital model of the lower arch form 10, determine the orthodontic treatment for the subject including forces to be applied onto the given lower tooth 15 to cause the given lower tooth 15 to move to the target position thereof. In specific non-limiting embodiments of the present technology, the orthodontic treatment may be determined (for example, by a processor 550 depicted in FIG. 5) as described in a co-owned U.S. Pat. No. 10,993,782-B1 issued on May 4, 2021, and entitled "SYSTEMS AND METHODS FOR DETERMINING A TOOTH TRAJECTORY", a content of which is hereby incorporated by reference in its entirety.

In alternative non-limiting embodiments of the present technology, the computer system 410 may be configured to receive the image data associated with the subject directly from an imaging device 430 communicatively coupled thereto. Broadly speaking, the processor 550 may be configured to cause the imaging device 430 to capture and/or process the image data of the lower teeth 12 and the periodontium (not depicted) of the subject. In certain non-limiting embodiments of the present technology, the image data may include, for example, one or more of: (1) images of external surfaces of respective crown portions of the lower teeth 12, (2) images of an external surface of the periodontium including those of the lower gingiva 14, the alveolar mandibular bone (not depicted), and images of superficial blood vessels and nerve pathways associated with the lower teeth 12; and (3) images of an oral region. By doing so, the imaging device 430 may be configured, for example, to capture image data of the lower arch form 10 of the subject. In another example, the imaging device may also be configured to capture and/or process image data of an upper arch form (not depicted) associated with the subject without departing from the scope of the present technology. It should be noted that the image data may include two-dimensional (2D) data and/or three-dimensional data (3D).

Further, in certain non-limiting embodiments of the present technology, the image data includes 2D data, from which 3D data may be derived, and vice versa.

In some non-limiting embodiments of the present technology, the imaging device 430 may comprise an intra-oral scanner enabling to capture direct optical impressions of each one of the lower arch form 10 and upper arch form 11 of the subject.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In yet other non-limiting embodiments of the present technology, the imaging device 430 can comprise a 3D laser scanner enabling to obtain a respective point cloud 3D digital model of each one of the lower arch form 10 and the upper arch form 11—such as by scanning a mold thereof and thus registering three-dimensional coordinates of points representative of the surface of the mold.

In a specific non-limiting example, the 3D laser scanner can be of one of the types available from LASER DESIGN of 5900 Golden Hills Drive, Minneapolis, Minn. 55416. It should be expressly understood that the desktop scanner can be implemented in any other suitable equipment.

Further, it is contemplated that the computer system 410 may be configured for processing of the received image data. The resulting image data of each one of the lower arch form 10 and then upper arch form 11 received by the computer system 410 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 410 may further comprise a corresponding computing environment.

Further, in certain non-limiting embodiments of the present technology, the system 400 may be configured to produced at least one configuration of the aligner 20 based on the planned orthodontic treatment as mentioned above. For example, in certain non-limiting embodiments of the present technology, the system 400 can be configured to produce an unfinished aligner (not depicted), for example, using a thermopriming process, in which a preform aligner (not depicted) is shaped on the mold of the lower arch form 10. Further, the system 400 can be configured to trim excess material along the cut line to produce an edge of the aligner 20.

In some non-limiting embodiments of the present technology, the system 400 can be configured to determine (or otherwise receive data indicative of) the cut line and mark the cut line on the unfinished aligner. To that end, the system 400 may further comprise a marking subsystem 440. It is not limited how the marking subsystem 440 may be implemented; however, in various non-limiting embodiments of the present technology, the marking subsystem 440 may include a marking head 442 for applying the cut line onto the unfinished aligner and a first robotic arm (not depicted) for holding and manipulating the unfinished aligner (not depicted) around the marking head 442. In some non-limiting embodiments of the present technology, the marking head 442 may further comprise a coloring material storage (not depicted) for storing a coloring material (such as ink, as an example) and a supply control block (not depicted). In some non-limiting embodiments of the present technology, the marking head 442 may be implemented as a laser apparatus configurable to scorch the cut line (not depicted) on the unfinished aligner (not depicted).

In certain non-limiting embodiments of the present technology, the system 400 may further be configured to detect the cut line applied on the unfinished aligner and cut along the cut line to produce the aligner 20. In this regard, the system 400 may further comprise a forming subsystem 450. In some non-limiting embodiments of the present technology, the forming subsystem 450 may include a second robotic arm (not depicted), at an end-effector of which there is installed a camera device 452. In some non-limiting embodiments of the present technology, the camera device 452 can be any appropriate digital camera configured to detect the cut line applied by the marking subsystem 440 described above onto the unfinished aligner, including, for example, but not limited to, a coupled-charged device camera (a CCD camera). Further, as mentioned above, the forming subsystem 450 may include the cutting device 454. Non limiting examples of the cutting device 454 may include a laser-based cutting device, a mechanical cutting device such as using a blade with a rotary or linear cutting action, and a water-jet based cutting device, as an example.

In some non-limiting embodiments of the present technology, both the marking subsystem 440 and the forming subsystem 450 of the system 400 may be implemented as described in a co-owned U.S. patent application Ser. No. 16/704,718 filed on Dec. 5, 2019, entitled "SYSTEMS AND METHODS FOR FORMING PERSONALIZED DENTAL APPLIANCES", the content of which is hereby incorporated by reference in its entirety.

Thus, the forming subsystem 450 may be configured to: (1) cause the camera device 452 to move around the unfinished aligner (not depicted) with the cut line (not depicted) applied thereon to detect the cut line and generating respective image data thereof; (2) receive the image data of the cut line; and (3) based on the received image data of the cut line, cause cutting, by the cutting device 454 the unfinished aligner along the cut line, thereby forming the aligner 20.

In other non-limiting embodiments of the present technology, the forming subsystem 450 may be configured for cutting the unfinished aligner without requiring detection of the cut line. Instead, the determined cut line is used to guide the cutting—for example, based on received data indicative of a position of the cut line within the unfinished aligner. In some non-limiting embodiments of the present technology, the data indicative of the position of the cut line within the unfinished aligner may include at least one of: Cartesian coordinates; angular data indicative of a cutting angle for cutting the unfinished aligner; and a distance from the cutting device 454, as an example.

Further, with reference to FIG. 5, there is depicted a schematic diagram of a computing environment 540 suitable for use with some implementations of the present technology. The computing environment 540 comprises various hardware components including one or more single or multi-core processors collectively represented by the processor 550, a solid-state drive 560, a random-access memory 570 and an input/output interface 580. Communication between the various components of the computing environment 540 may be enabled by one or more internal and/or external buses 590 (e.g. a PCI bus, universal serial bus, IEEE 1394 "Firewire" bus, SCSI bus, Serial-ATA bus, ARINC bus, etc.), to which the various hardware components are electronically coupled.

The input/output interface 580 allows enabling networking capabilities such as wire or wireless access. As an example, the input/output interface 580 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 580 may implement specific physical layer and data link layer standard such as Ethernet, Fibre Channel, Wi-Fi™ or Token Ring™. The specific physical layer and the data link layer may provide a base for a full network protocol stack, allowing communication among small groups of computers on the same local area network (LAN) and large-scale network communications through routable protocols, such as IP.

According to implementations of the present technology, the solid-state drive 560 stores program instructions suitable for being loaded into the random-access memory 570 and executed by the processor 550, according to certain aspects and embodiments of the present technology. For example, the program instructions may be part of a library or an application.

In some non-limiting embodiments of the present technology, the computing environment 540 is implemented in a generic computer system, which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 540 can be implemented may be envisioned without departing from the scope of the present technology.

Referring back to FIG. 4, the computer system 410 has at least one interface device 420 for providing an input or an output to a user of the system 400, the interface device 420 being in communication with the input/output interface 580. In the embodiment of FIG. 4, the interface device is a screen 422. In other non-limiting embodiments of the present technology, the interface device 420 may be a monitor, a speaker, a printer or any other device for providing an output in any form such as an image form, a written form, a printed form, a verbal form, a 3D model form, or the like.

In the depicted embodiments of FIG. 4, the interface device 420 also comprises a keyboard 424 and a mouse 426 for receiving input from the user of the system 400. Other interface devices 420 for providing an input to the computer system 410 can include, without limitation, a USB port, a microphone, a camera or the like.

The computer system 410 may be connected to other users, such as through their respective clinics, through a server (not depicted). The computer system 410 may also be connected to stock management or client software which could be updated with stock when the orthodontic treatment has been determined and/or schedule appointments or follow-ups with clients, for example.

Image Data

As alluded to above, according to certain non-limiting embodiments of the present technology, the processor 550 may be configured to: (1) receive the respective 3D digital model of a current configuration of the lower arch form 10 including the 3D digital model of the given tooth; (2) determine, based on the respective 3D digital model, the position for the orthodontic attachment 304 on the surface of the given tooth; and optionally (3) and determine, based on the position of the orthodontic attachment, a configuration of the cut line for further use in producing the respective configuration of the aligner 20, as mentioned above.

Figure 6:
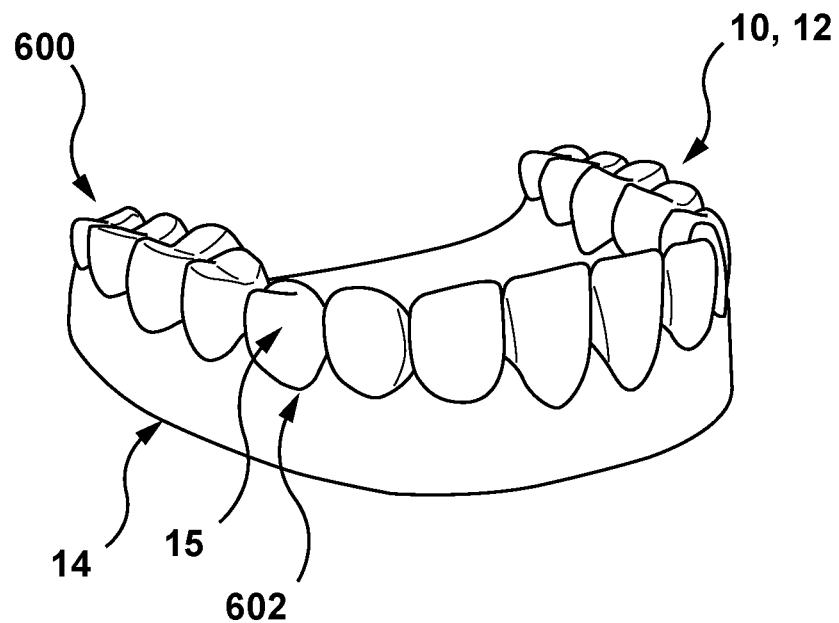
FIG. 6 depicts a 3D digital model of the lower arch form of the subject present in FIG. 1 used, by the processor of FIG. 5, to determine the position for the orthodontic attachment of FIG. 3A, in accordance with certain non-limiting embodiments of the present technology.
Figure 7:
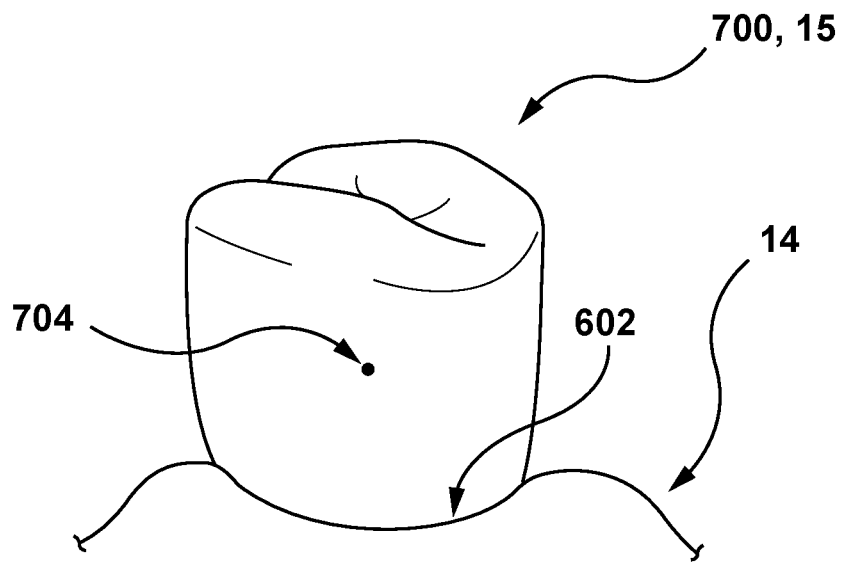
FIG. 7 depicts a 3D digital model of the given tooth of the subject isolated, by the processor of FIG. 5, from the 3D digital model of FIG. 6, in accordance with certain non-limiting embodiments of the present technology.

With reference to FIG. 6, there is schematically depicted a perspective view of an arch form 3D digital model 600 of the lower arch form 10 used, by the processor 550, for determining the position for the orthodontic attachment 304 on the surface of the given lower tooth 15, in accordance with certain non-limiting embodiments of the present technology.

In some non-limiting embodiments of the present technology, the processor 550 may be configured to receive, from the imaging device 430, the arch form 3D digital model 600 comprising a respective plurality of mesh elements (not depicted) representative of a surface of the lower arch form 10. For example, the imaging device 430 can be configured to generate the plurality of mesh elements including, without limitation, triangular mesh elements, quadrilateral mesh elements, convex polygonal mesh elements, or even concave polygonal mesh elements, as an example, without departing from the scope of the present technology.

However, in those embodiments where the imaging device 430 is the 3D laser scanner, the arch form 3D digital model 600 comprises a respective 3D point cloud representative of the surface of the lower arch form 10.

As noted above, according to the non-limiting embodiments of the present technology, the lower arch form 10 comprises the lower teeth 12 (also referred to herein as "mandibular teeth") and the lower gingiva 14. As it can be appreciated, the lower teeth 12 are represented, in the arch form 3D model 600, by respective crown portions associated therewith.

It should be expressly understood that, although the description herein below will be given in respect of the lower arch form 10 of the subject (and associated therewith the lower teeth 12 and the lower gingiva 14) for the sake of clarity and simplicity thereof, and in no way as a limitation, the non-limiting embodiments of the present technology can also apply to the upper teeth 13 of the subject with certain alterations, which will be explicitly indicated below where necessary.

Further, according to certain non-limiting embodiments of the present technology, based on the arch form 3D digital model 600, the processor 550 can be configured to generate a 3D digital model of the given lower tooth 15. With continued reference to FIG. 6 and with reference to FIG. 7, there is depicted a schematic diagram of a tooth 3D digital model 700 of the given lower tooth 15, in accordance with certain non-limiting embodiments of the present technology.

In some non-limiting embodiments of the present technology, to generate the tooth 3D digital model 700, the processor 550 can be configured to isolate a portion of the arch form 3D digital model 600 representative of the crown portion of the given lower tooth 15.

How the processor 550 can be configured to isolate the portion of the arch form 3D digital model 600 representative of the crown portion of the lower tooth 15 is not limited; and, in some non-limiting embodiments of the present technology, the processor 550 can be configured to apply, to the arch form 3D digital model 600, one or more automatic tooth segmentation approaches described in a co-owned U.S. Pat. No. 10,950,061-B1 issued on Mar. 16, 2021, entitled "SYSTEMS AND METHODS FOR PLANNING AN ORTHODONTIC TREATMENT", content of which is incorporated herein by reference in its entirety.

More specifically, to generate the tooth 3D digital model 700 of the given lower tooth 15, the processor 550 may be configured to: (i) acquire the arch form 3D digital model 600 of the lower arch form 10 of the subject, the arch form 3D digital model 600 comprising a defined portion forming part of a surface of the given lower tooth 15, and at least one undefined portion not forming part of the surface of the given lower tooth 15; the arch form 3D digital model 600 comprising the plurality of mesh elements having a plurality of vertices comprising: constrained vertices associated with the defined portion, each constrained vertex having a normal constrained vertex vector; unconstrained vertices initially associated with the undefined portion, each unconstrained vertex having a normal unconstrained vertex vector; (ii) generate a set of confirmed constrained vertices, including the constrained vertices associated with the defined portion, representative of the crown portion of the given lower tooth 15 by: (iii) iteratively, for a given constrained vertex, identifying at least one associated unconstrained vertex which is adjacent to the given constrained vertex in the plurality of mesh elements; (iv) determining an angular difference between the normal constrained vertex vector of the given constrained vertex and the normal unconstrained vertex vector of the at least one associated unconstrained vertex; (v) in response to the angular difference being equal to or below a predetermined threshold value: identifying the at least one associated unconstrained vertex to be a constrained vertex associated with the defined portion for inclusion in the set of confirmed constrained vertices; (vi) in response to the angular difference being above the predetermined threshold value: identifying the at least one associated unconstrained vertex to be an unconstrained vertex associated with the undefined portion for exclusion from the set of confirmed constrained vertices.

Further, according to certain non-limiting embodiments of the present technology, the processor 550 can be configured to determine, based on the arch form 3D digital model 600 of the lower arch form 10, a tooth-gingiva segmentation loop 602 indicative of a boundary between the crown portion of the given lower tooth 15 and the lower gingiva 14.

In some non-limiting embodiments of the present technology, the processor 550 can be configured to determine the tooth-gingiva segmentation loop 602 as a closed curve extending along an edge of the portion of the arch form 3D digital model 600 representative of the crown portion of the given lower tooth 15, determined as described above with reference to FIG. 7.

In other non-limiting embodiments of the present technology, the processor 550 may be configured to obtain the tooth-gingiva segmentation loop 602 having been previously generated by third-party software, based on the arch form 3D digital model 600, and data indicative thereof may have been stored in a data format, in which the processor 550 may be configured to receive it, for example, via the input/output interface 580.

In yet other non-limiting embodiments of the present technology, the tooth-gingiva segmentation loop 602 may be generated manually, for example, by a practicing clinician involved in the determining the orthodontic treatment. For example, a practicing clinician involved in the determining the orthodontic treatment for the subject may manually apply the tooth-gingiva segmentation loop 602 onto the arch form 3D digital model 600, using respective suitable software, and the processor 550 may further be configured to receive the arch form 3D digital model 600, and detect the tooth-gingiva segmentation loop 602 applied thereon.

Further, as will become apparent from the description provided hereinbelow, in at least some non-limiting embodiments of the present technology, the determining the position for the orthodontic attachment 304 on the surface of the given lower tooth 15 can include determining, in the tooth 3D digital model, a respective tooth reference point therewithin indicative of a position thereof relative to other ones of the lower teeth 12, such as a tooth reference point 704. It is not limited how the tooth reference point 704 can be determined, and in various non-limiting embodiments of the present technology, can comprise a specific point equally representative of each one of the lower teeth 12, such as that representative of a common anatomical feature of each one of the lower teeth 12, including, for example, a middle point of a respective crown portion thereof, a cusp tip thereof, one of developmental grooves thereof, and the like.

For example, in some non-limiting embodiments of the present technology, the tooth reference point 704 can include a geometric center of mass associated with the given lower tooth 15, such as that determined considering the given lower tooth 15 as a solid physical object.

However, in other non-limiting embodiments of the present technology, the center point 704 can be determined as being a center of resistance (CR) point associated with the given lower tooth 15. For example, a location of the CR point within the given lower tooth 15 can be determined based on the tooth 3D digital model 700 as described in a co-owned U.S. Pat. No. 10,856,954-B1 issued on Dec. 8, 2020 and entitled "SYSTEMS AND METHODS FOR DETERMINING TOOTH CENTER OF RESISTANCE", the content of which is hereby incorporated by reference in its entirety. More specifically, in these embodiments, the processor 550 can be configured to: (i) obtain the tooth 3D digital model 700; (ii) identify an internal tooth reference point within the tooth 3D digital model 700, the internal tooth reference point corresponding to a mesiodistal center of the crown portion of the given lower tooth 15, the identifying the internal tooth reference point comprising: obtaining a mesial point on a mesial side of the crown portion, and a distal point on a distal side of the crown portion; generating a mesiodistal line joining the mesial point and the distal point; identifying the mesiodistal center as a midpoint on the mesiodistal line; (iii) determine a reference plane in the tooth 3D digital model 700, the reference plane being perpendicular to the mesiodistal line and extending through the mesiodistal center; (iv) determine an intersection curve based on an intersection of the reference plane and the tooth 3D digital model 700, the intersection curve following a shape of the surface of the tooth 3D digital model 700 at the reference plane; (v) determine a tooth axis of the given lower tooth 15 based on the intersection curve; (vi) determine a crown height of the crown portion of the given tooth based on the determined tooth axis; and (vii) determine the CR point of the given lower tooth 15 based on the determined crown height and the determined tooth axis.

Thus, having obtained the above data, the processor 550 can be configured to determine the position for the orthodontic attachment 304 on the surface of the given lower tooth 15, which will now be described with reference to FIGS. 9A to 13B.

Determining the Work Area

First, as mentioned above, according to certain non-limiting embodiments of the present technology, the processor 550 can be configured to determine the work area 910 on the surface of the given lower tooth 15, within which the orthodontic attachment 304 would be positioned. In some non-limiting embodiments of the present technology, the processor 550 can be configured to determine the work area 910 as corresponding to an area on the surface of the given lower tooth 15 having a predetermined curvature.

Figure 8:
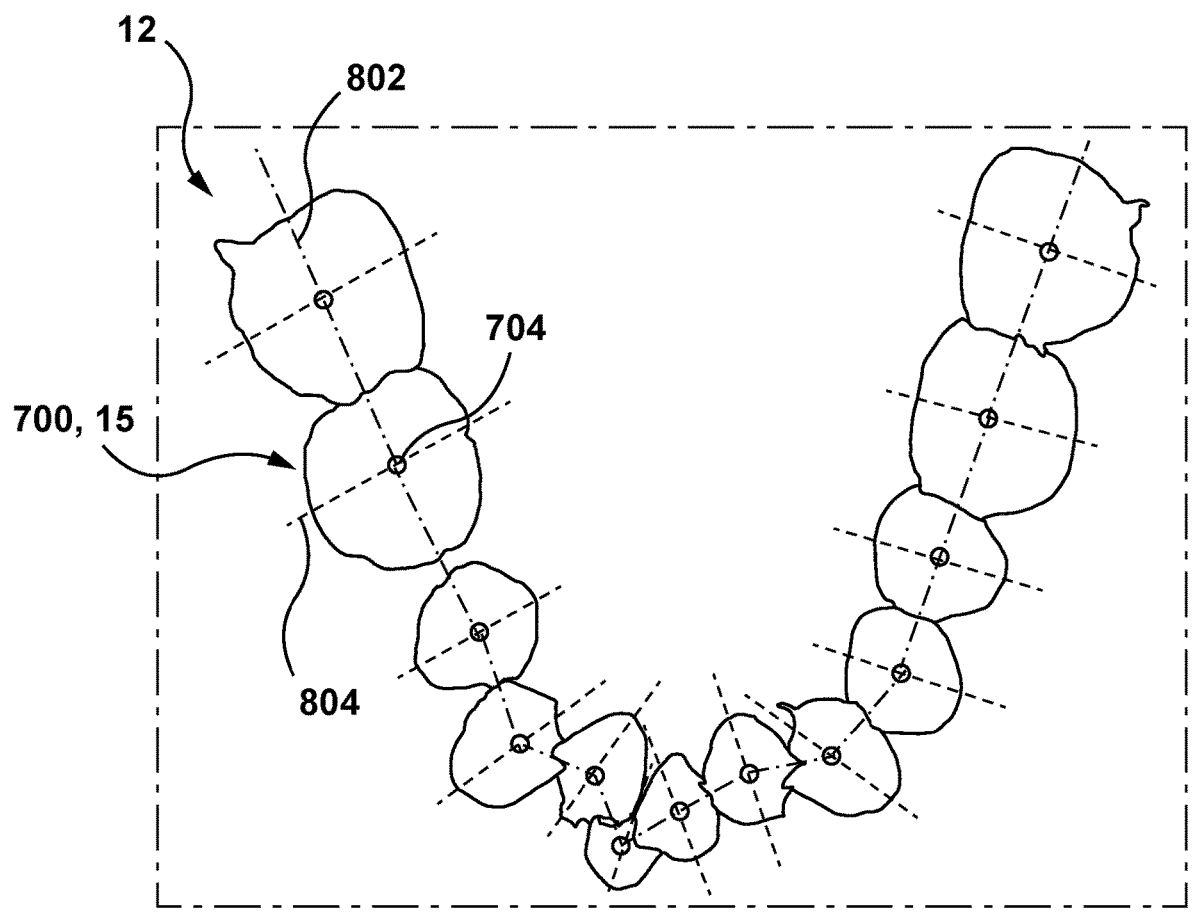
FIG. 8 depicts a schematic diagram of a top view of the 3D digital model of the lower arch form of FIG. 6 illustrating an approach to determining a jaw curve extending through the subject's teeth, in accordance with certain non-limiting embodiments of the present technology.

To that end, according to certain non-limiting embodiments of the present technology, the processor 550 can be configured to determine a jaw curve associated with the lower teeth 12. With reference to FIG. 8, there is depicted a top view of the arch form 3D digital model 600 illustrating an approach for determining, by the processor 550, a lower jaw curve 802, in accordance with certain non-limiting embodiments of the present technology.

According to certain non-limiting embodiments of the present technology, the processor 550 can be configured to determine the lower jaw curve 802 by sequentially joining respective tooth reference points associated with each one of the lower teeth 12, such as the tooth reference point 704 associated with given lower tooth 15, as described above.

It should be noted that it is not limited how the processor 550 can be configured to join the respective tooth reference points. For example, in some non-limiting embodiments of the present technology, the processor 550 can be configured to join the respective tooth reference points associated with the lower teeth 12 with linear segments. However, in other non-limiting embodiments of the present technology, the processor 550 can be configured to join the respective tooth reference points with curve segments, such as those defined by a polynomial function, including, for example, a spline function, a Bezier curve function, and the like. In additional non-limiting embodiments of the present technology, after joining the respective tooth reference points, the processor 550 can further be configured to smooth joints therebetween using any suitable curve smoothing algorithm, such as a local regression smoothing algorithm, a Kernel smoothing algorithm, and the like.

Further, to analyze the curvature of the side surface of the given lower tooth 15, the processor 550 can be configured to determine, for each one of the lower teeth 12 a respective reference plane intersecting the lower jaw curve 802 in the respective tooth reference point—such as a reference plane 804 extending through the tooth reference point 704 associated with the given lower tooth 15. For example, in some non-limiting embodiments of the present technology, the processor 550 can be configured to determine the reference plane 804 as being perpendicular to the lower jaw curve 802 (or to a tangent thereof at the reference point 704).

Further, the processor 550 can be configured to analyze the curvature of the side surface of the given lower tooth 15 relative to the reference plane 804. More specifically, depending on a particular side of the given lower tooth 15 onto which the orthodontic attachment 304 is to be attached thereto, such as a buccal or lingual side thereof, the processor 550 can be configured to determine an angular difference between the reference plane 804 and a respective normal vector defined at a each vertex of the tooth 3D digital model 700 on a buccal or lingual side thereof relative to the lower jaw curve 802.

Figure 9A:
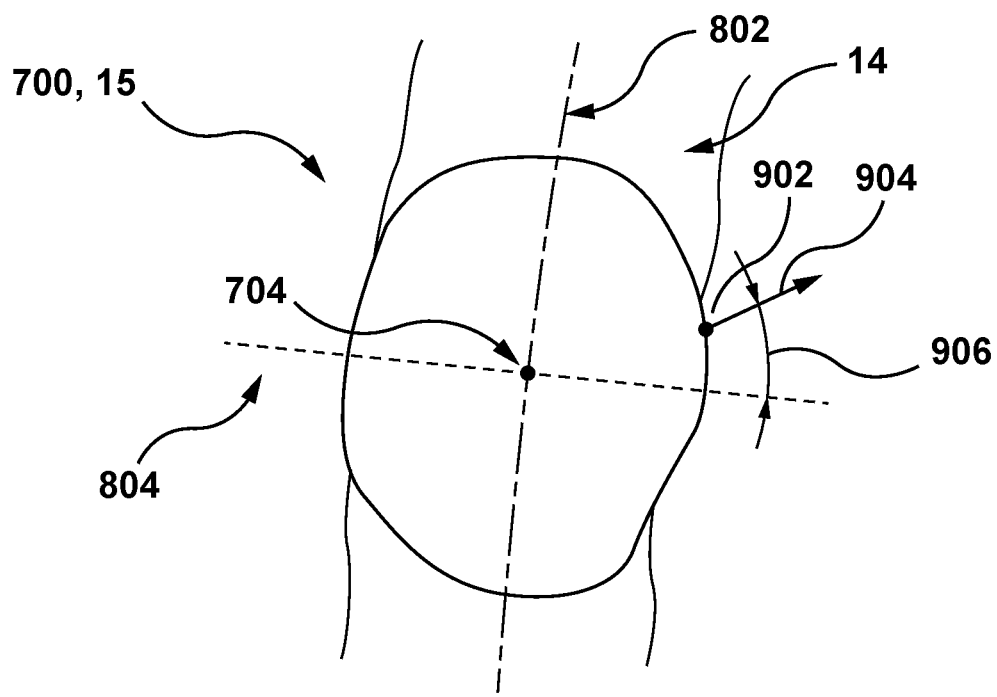
FIG. 9A depicts a schematic diagram of a top view of the 3D digital model of the given tooth illustrating an approach for determining, by the processor of FIG. 5, a work area on a surface of the given tooth for positioning thereon the orthodontic attachment of FIG. 3B, in accordance with certain non-limiting embodiments of the present technology.
Figure 9B:
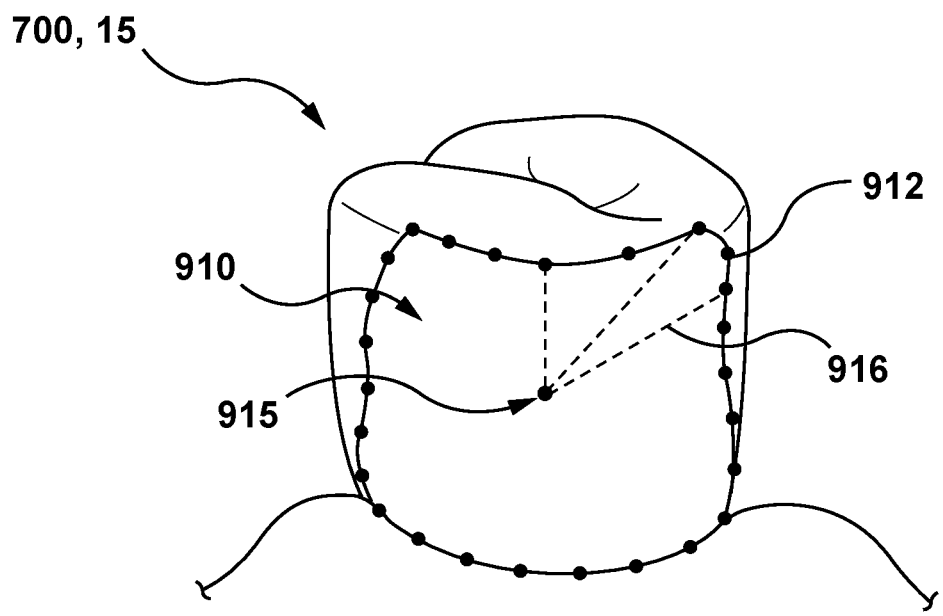
FIG. 9B depicts a schematic diagram of a step for determining, by the processor of FIG. 5, a reference vertex within the work area of FIG. 9A representative of a first vertical boundary for a positioning space for the orthodontic attachment of FIG. 3B on the surface of the given tooth, in accordance with certain non-limiting embodiments of the present technology.

With reference to FIGS. 9A and 9B, there is depicted a schematic diagram of a top and side view of the tooth 3D digital model 700 illustrating an approach for determining, by the processor 550, the work area 910 on the surface of the given lower tooth 15, in accordance with certain non-limiting embodiments of the present technology.

More specifically, in some non-limiting embodiments of the present technology, the processor 550 can be configured to determine a respective angular difference 906 between a normal vector 904 to the surface of the tooth 3D digital model 700 at a given vertex 902 representative of the buccal side of the given lower tooth 15, for example. Further, in response to determining that the respective angular difference 906 is greater than a predetermined angular difference threshold value (being, for example, 60 or 75 degrees), the processor 550 can be configured to remove the given vertex 902 from further consideration, that is, reject from inclusion thereof in vertices representative of the work area 910. By contrast, in response to determining that the respective angular difference 906 is lower than or equal to the predetermined angular difference threshold, the processor 550 can be configured to determine the given vertex 902 as being representative of the work area 910. Thus, by analyzing the curvature of the buccal side of the given lower tooth 15 in a such a way, the processor 550 can be configured to determine the work area 910 for positioning the orthodontic attachment 304 therewithin.

Determining a Position for the Attachment

Further, the processor 550 can be configured to determine, within the work area 910, the positioning space 1210 on which the orthodontic attachment 304 is to be attached to the given lower tooth 15. To that end, the processor 550 can be configured to: (1) determine a first vertical boundary for the positioning space 1210; (2) determine a second vertical boundary for the positioning space 1210; (3) retrieve a respective pattern representative of a shape of the base portion 306 of the orthodontic attachment 304; and (4) fit the respective pattern within the work area 910 between the first vertical boundary and the second vertical boundary.

According to certain non-limiting embodiments of the present technology, the processor 550 can be configured to determine the first vertical boundary as a boundary towards the crown portion of the given lower tooth 15, that is, in the orientation of FIG. 9B, the first vertical boundary can be defined as being an upper boundary for the positioning space.

In this regard, with continued reference to FIG. 9B, according to certain non-limiting embodiments of the present technology, the processor 550 can be configured to determine, within the work area 910, a reference vertex 915 representative of the first vertical boundary of the positioning space 1210. It is not limited how the processor 550 can be configured to determine the reference vertex 915. For example, the processor 550 can be configured to determine the reference vertex 915 as being a center of the work area 910.

However, in other non-limiting embodiments of the present technology, to determine the reference vertex 915, the processor 550 can be configured to: (i) identify a plurality of contour vertices 912 defining a contour of the work area 910; and (ii) determine the reference vertex 915 as being a vertex of the work area 910 that is most distant from all of the plurality of contour vertices 912. In some non-limiting embodiments of the present technology, the processor 550 can be configured to determine such a vertex by determining a vertex of the work area 910 from which a summation of all distance values therefrom to each one of the plurality of contour vertices 912, such as a given distance value 916, is maximum. To that end, the processor 550 can be configured to apply a Dijkstra algorithm, as an example.

Further, according to certain non-limiting embodiments of the present technology, based on a predetermined rule, the processor 550 can be configured to determine the second vertical boundary for the positioning space 1210 as corresponding to the tooth-gingiva segmentation loop 602 associated with the given lower tooth 15, that is, in the orientation of FIG. 9B, the second vertical boundary can be defined as a lower boundary for the positioning space 1210 for the orthodontic attachment 304.

Figure 10A:
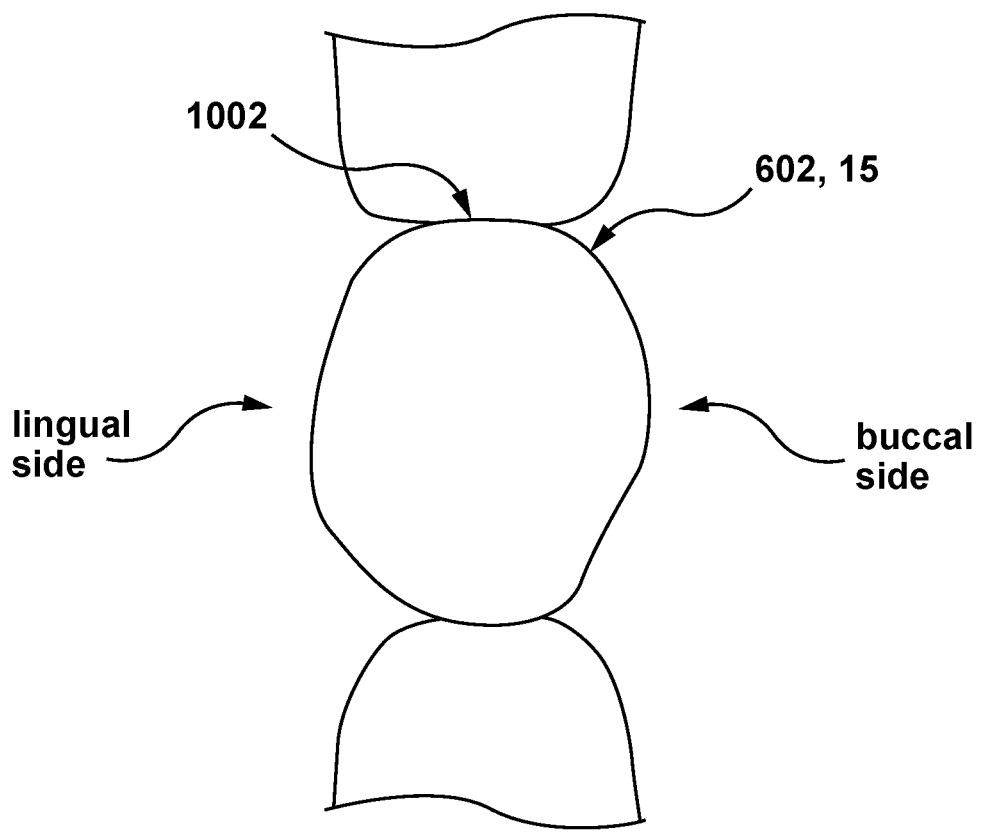
FIGS. 10A and 10B depict a top view of a tooth-gingiva segmentation loop between the given tooth and its surrounding gingiva illustrating an approach of determining, by the processor of FIG. 5, a plurality of additional reference vertices representative of a second vertical boundary for the positioning space for the orthodontic attachment of FIG. 3B, in accordance with certain non-limiting embodiments of the present technology.
Figure 10B:
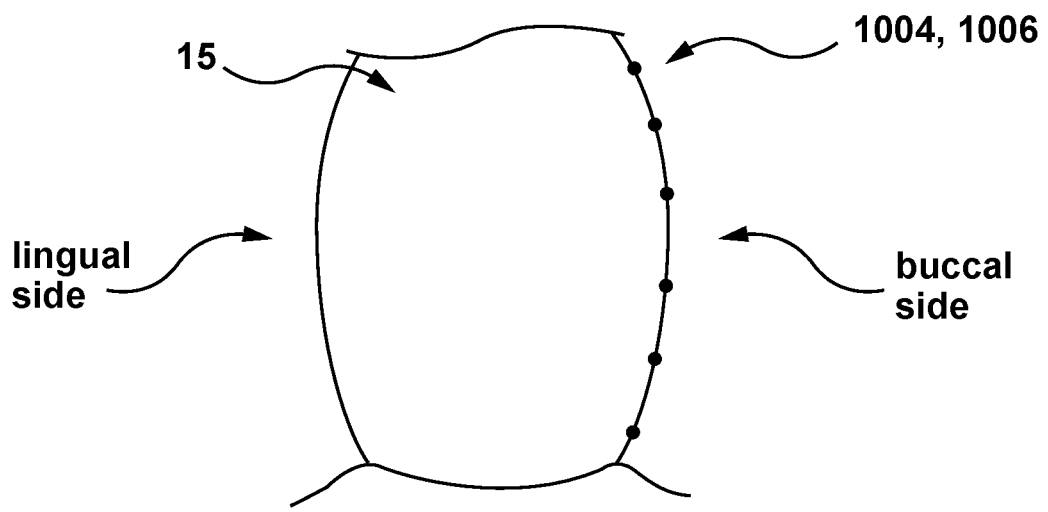

With reference to FIGS. 10A and 10B, there is depicted a top view of the tooth-gingiva segmentation loop 602 illustrating an approach of determining, by the processor 550, a plurality of additional reference vertices 1006 representative of the second vertical boundary for the positioning space 1210 for the orthodontic attachment 304, in accordance with certain non-limiting embodiments of the present technology.

First, in some non-limiting embodiments of the present technology, the processor 550 can be configured to identify, along the tooth-gingiva segmentation loop 602, portions thereof that are common to teeth neighboring the given lower tooth 15—such as a given common portion 1002 of the tooth-gingiva segmentation loop 602.

For example, in some non-limiting embodiments of the present technology, the processor 550 can be configured to determine the given common portion 1002 as a portion of the tooth-gingiva segmentation loop 602 extending along a respective one of a mesial and distal portion of the side surface of the given lower tooth 15. To that end, the processor 550 can be configured to analyze the curvature of the side surface of the given lower tooth 15, relative to the reference plane 804, to determine the buccal and lingual portions thereof, as described above with reference to FIGS. 9A and 9B with respect to determining the work area 910. Further, the processor 550 can be configured to determine remaining portions along the side surface of the given lower tooth 15 as being the mesial and distal portions, respectively.

However, in other non-limiting embodiments of the present technology, the processor can be configured to determine the given common portion 1002 as being a portion of the tooth-gingiva segmentation loop 602 that extends along a respective crown contact area between the given lower tooth 15 and one of the teeth neighboring thereto. More specifically, in these embodiments, using the arch form 3D digital model 600, the processor 550 can be configured to: (1) identify areas of the given lower tooth 15 where it touches at least one of the teeth adjacent thereto; and (2) project vertices of the tooth 3D digital model 700 representative of such areas to the tooth-gingiva segmentation loop 602, thereby identifying the given common portion 1002 thereof.

Further, the processor 550 can be configured to remove the given common portion 1002 of the tooth-gingiva segmentation loop 602 from further consideration, thereby generating a refined tooth-gingiva segmentation contour 1004, as schematically depicted in FIG. 10A, in accordance with certain non-limiting embodiments of the present technology. Further, along a segment of the refined tooth-gingiva segmentation contour 1004 corresponding to the work area 910 determined above, which in the depicted example is a buccal segment, the processor 550 can be configured to determine the plurality of additional reference vertices 1006.

However, in other non-limiting embodiments of the present technology, the processor 550 can be configured to identify the plurality of additional reference vertices 1006 among vertices of the plurality of contour vertices 912 of the work area 910 defined along the tooth-segmentation loop 602.

Further, it is not limited how the processor 550 can be configured to determine a number of vertices in the plurality of additional reference vertices 1006. For example, in some non-limiting embodiments of the present technology, as will become apparent from the description provided below, the processor 550 can be configured to determine the number of vertices of the plurality of additional reference vertices 1006 based on at least one of a complexity of a shape (including a number of bends, for example) and dimensions of the base portion 306 of the orthodontic attachment 304 to be attached to the given lower tooth 15. For example, the processor 550 can be configured to determine the plurality of additional reference vertices including 3, 4, 5, or 10 vertices, for example.

However, in other non-limiting embodiments of the present technology, the processor 550 can be configured to determine the number of vertices in the plurality of additional reference vertices 1006 based on a trade-off between accuracy of defining the positioning space for the orthodontic attachment 304 and available computational resources of the processor 550.

Further, it is not limited how the plurality of additional reference vertices 1006 can be distributed along the work area 910; and in some non-limiting embodiments of the present technology, the processor 550 can be configured to distribute the plurality of additional reference vertices 1006 uniformly along the work area 910.

Thus, having determined, in the tooth 3D digital model 700 of the given lower tooth 15, the reference vertex 915 and the plurality of additional reference vertices 1006, respectively representative of the first vertical boundary and the second vertical boundary of the positioning space 1210 for the orthodontic attachment 304, the processor 550 can be configured to determine a shape of the positioning space 1210 on the surface of the given lower tooth 15 for accommodating thereon the orthodontic attachment 304.

To that end, in some non-limiting embodiments of the present technology, the processor 550 can be configured to: (1) receive data representative of the orthodontic attachment 304 including, for example, that of the shape and dimensions of the base portion 306 thereof, as described above; (2) retrieve, based on the data of the orthodontic attachment 304, for example, from the solid-state drive 560 of the computing environment 540, data representative of a respective pattern corresponding in shape to base portion 306 of the orthodontic attachment 304; and (3) fit the respective pattern on the surface of the tooth 3D digital model 700 between the first and second vertical boundaries determined.

According to certain non-limiting embodiments of the present technology, the processor can be configured to receive the data representative of the orthodontic attachment 304 from a dental practitioner (such as an orthodontist) involved in determining the orthodontic treatment for the subject. However, in other non-limiting embodiments of the present technology, such data can be pre-uploaded to the processor 550 as part of program instructions causing the processor 550 to execute the present methods.

Figure 11:
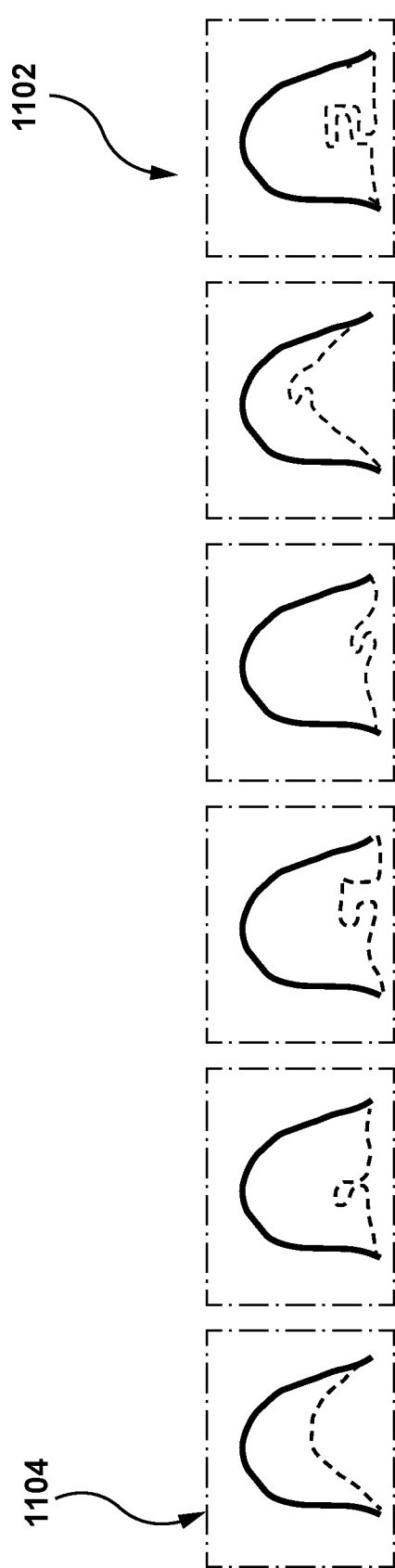
FIG. 11 depicts a schematic diagram of a plurality of patterns available for selection, by the processor of FIG. 5, for defining a shape of the positioning space for the orthodontic attachment of FIG. 3B on the surface of the given tooth, in accordance with certain non-limiting embodiments of the present technology.
Figure 12A:
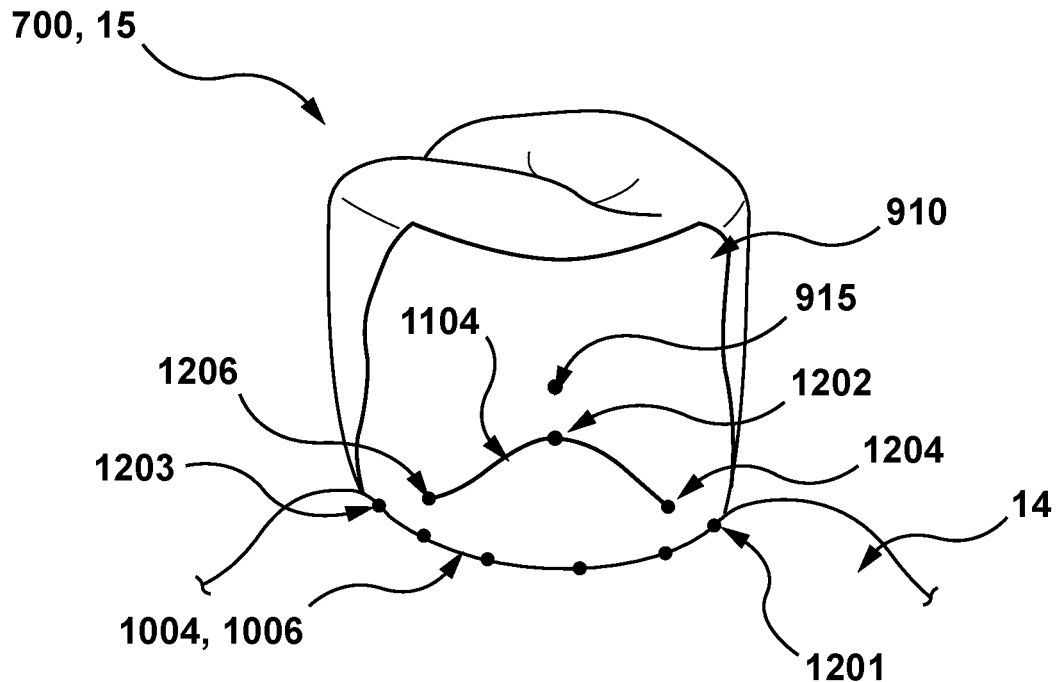
FIGS. 12A and 12B depict schematic diagrams of one approach to fitting, by the processor of FIG. 5, a given pattern of the plurality of patterns of FIG. 11 within the surface of the 3D digital model of the given tooth to define the positioning space for the orthodontic attachment of FIG. 3B on the surface of the given tooth, in accordance with certain non-limiting embodiments of the present technology.
Figure 12B:
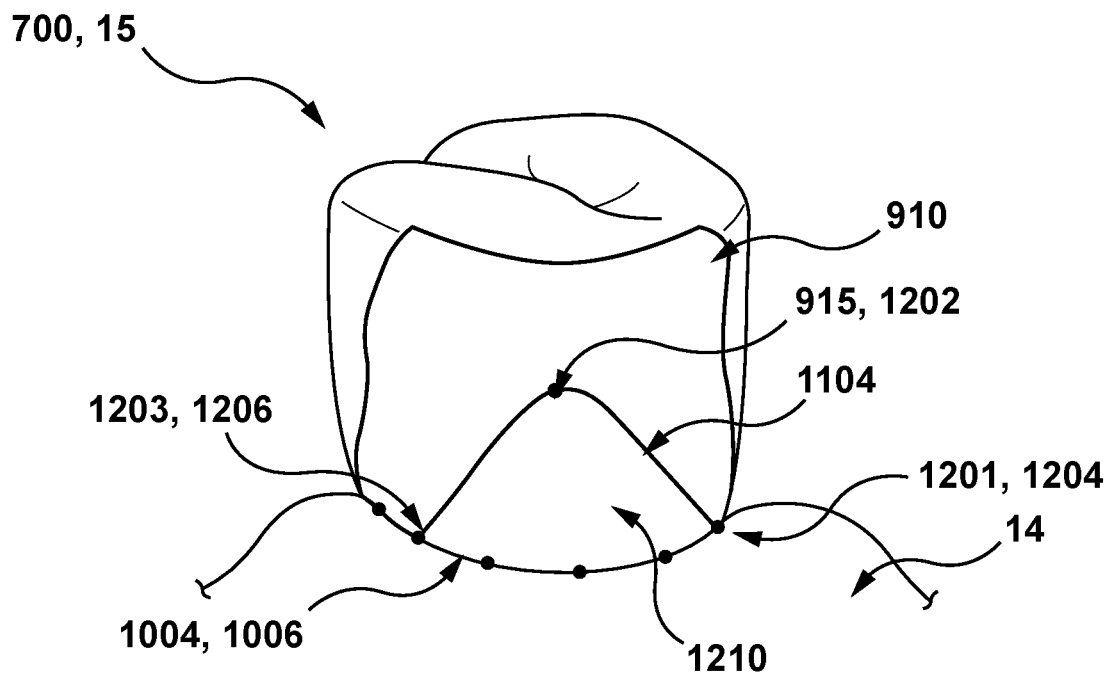

With reference to FIG. 11, there is depicted a schematic diagram of a plurality of patterns 1102 available for selection, by the processor 550, for defining the shape of the positioning space 1210 for the orthodontic attachment 304 on the surface of the given lower tooth 15, in accordance with certain non-limiting embodiments of the present technology.

For example, based on the shape of the base portion 306 of the orthodontic attachment 304, the processor 550 can be configured to select a given pattern 1104 to further define the positioning space 1210 for the orthodontic attachment 304. Further, with reference to FIGS. 12A and 12B, there are depicted schematic diagrams of an approach to fitting, by the processor 550, the given pattern 1104 within the surface of the tooth 3D digital model 700, thereby defining the positioning space 1210 for the orthodontic attachment 304 on the surface of the given lower tooth 15, in accordance with certain non-limiting embodiments of the present technology.

As it can be appreciated, the given pattern 1104 has (i) at least one peak point towards the crown portion of the given lower tooth 15, that is, a crown peak point 1202; and (ii) at least one peak towards the lower gingiva 14, that is, a first gingiva peak point 1204 and a second gingiva peak point 1206. Thus, in accordance with certain non-limiting embodiments of the present technology, to define the positioning space 1210, the processor 550 can be configured to apply at least one transformation to the given pattern 1104 such that: (1) the crown peak point 1202 matches the reference vertex 915; and (2) the first gingiva peak point 1204 and the second gingiva peak point 1206 match respective ones of the plurality of additional reference vertices 1006, such as a first additional reference vertex 1201 and a second additional reference vertex 1203.

It is not limited how the processor 550 can be configured to determine the first additional reference vertex 1201 and the second additional reference vertex 1203; and in some non-limiting embodiments of the present technology, the processor 550 can be configured to determine them based on the dimensions of the base portion 306 of the orthodontic appliance 304. More specifically, the processor 550 can be configured to determine the first additional reference vertex 1201 and the second additional reference vertex 1203 such that the positioning space 1210 so defined has minimal dimensions allowing accommodating therein the base portion 306 of the orthodontic attachment 304.

In some non-limiting embodiments of the present technology, the processor 550 can be configured to apply one or more different transformations to the given pattern 1104 for fitting it within the surface of the tooth 3D digital model 700, which can include, without limitation, one or more of: translation, rotation, reflection, and scaling (e.g. stretching and/or shrinking).

Figure 13A:
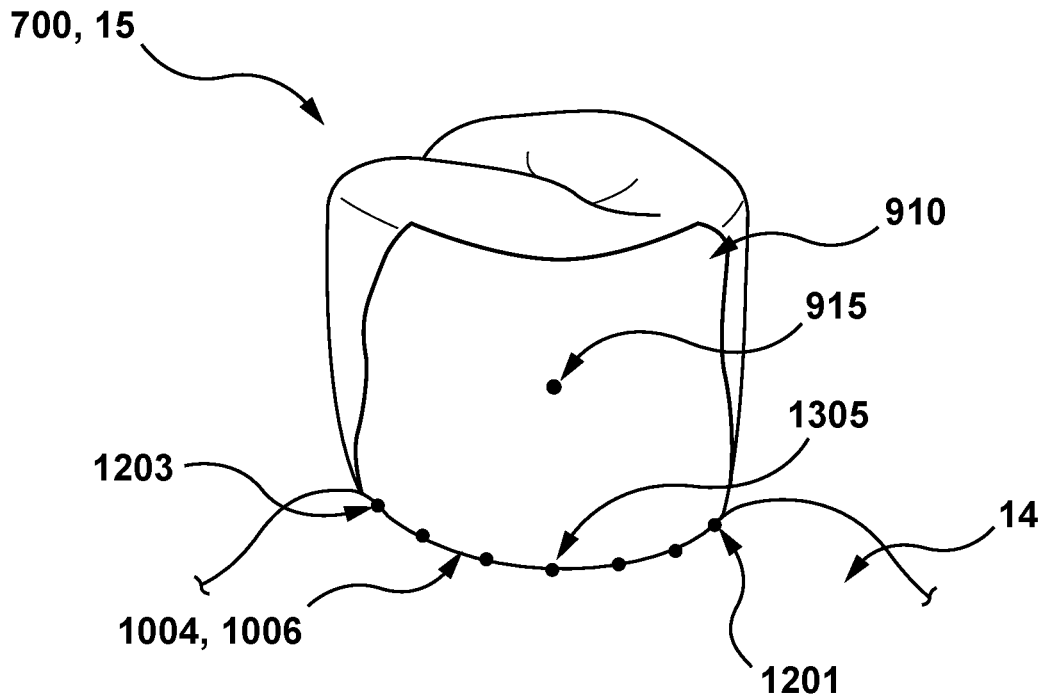
FIGS. 13A and 13B depict schematic diagrams of another approach to fitting, by the processor of FIG. 5, a given pattern of the plurality of patterns of FIG. 11 within the surface of the 3D digital model of the given tooth to define the positioning space for the orthodontic attachment of FIG. 3B on the surface of the given tooth, in accordance with certain non-limiting embodiments of the present technology.
Figure 13B:
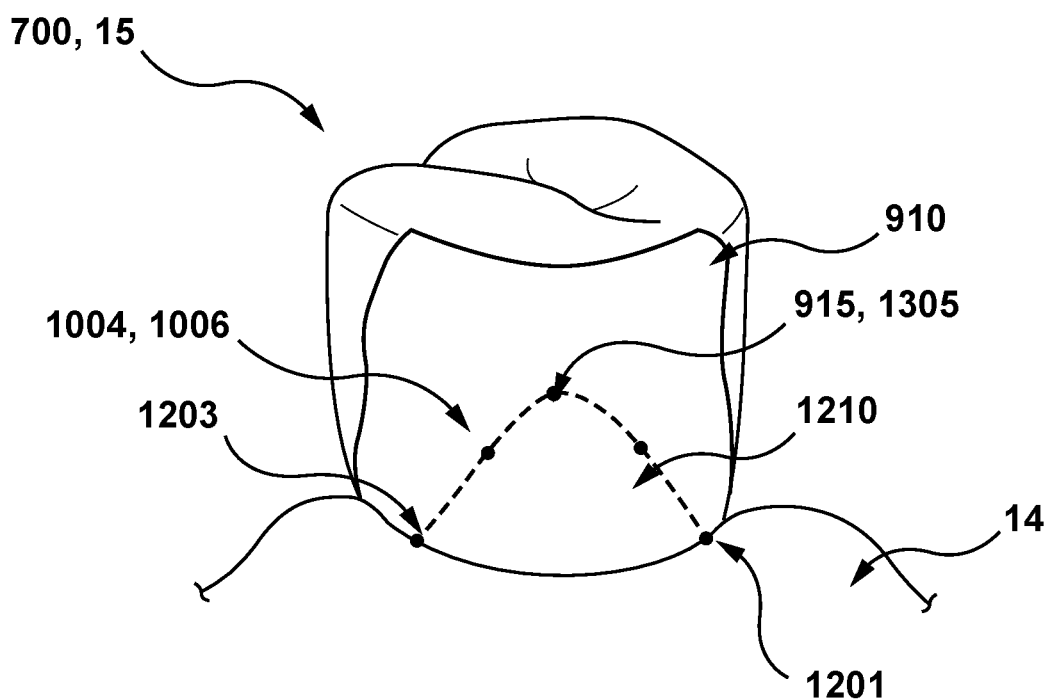

However, in other non-limiting embodiments of the present technology, the processor 550 can be configured to define the positioning space 1210 differently. With reference to FIGS. 13A and 13B, there are depicted schematic diagrams of another approach to fitting, by the processor 550, the given pattern 1104 within the surface of the tooth 3D digital model 700 to define the positioning space 1210 for the orthodontic attachment 304 on the surface of the given lower tooth 15, in accordance with certain non-limiting embodiments of the present technology.

Broadly speaking, in these embodiments, the processor 550 can be configured to shape the positioning space 1210 from the plurality of additional reference vertices 1006. To that end, the processor 550 can be configured to consider the plurality of additional reference vertices 1006 as defining segments of a continuous curve, such that a modification to any of the so defined segments, such as stretching, translation, or rotation, would not cause the curve to break.

Thus, the processor 550 can be configured to identify, based on considerations of symmetry of the given pattern 1104, for example, at least one of the plurality of additional reference vertices 1006 to displace towards the reference vertex 915—such as a given additional reference vertex 1305. Further, the processor 550 can be configured to displace the given additional reference vertex 1305 along the surface of the tooth 3D digital model 700 towards the reference vertex 915 until the former matches the latter, while retaining initial positions of edge vertices, that is, in the present example, the first and second additional reference vertices 1201, 1203. By doing so, the processor 550 can be configured to cause displacement to other ones of the plurality of additional reference vertices 1006 scaling distances therebetween proportionally to a displacement distance of the given additional reference vertex 1305, as an example.

Further, in additional non-limiting embodiments of the present technology, the processor 550 can be configured to join the plurality of additional reference vertices 1006, so re-arranged within the work area 910, either with straight segments or curve segments, such as splines, as an example.

Thus, the processor 550 can be configured to define the positioning space 1210 on the surface of the given lower tooth 15 configured for accommodating the base portion 306 of the orthodontic attachment 304.

Determining Configuration of the Orthodontic Appliance

As noted hereinabove, in accordance with certain non-limiting embodiments of the present technology, based on data of the positioning space 1210, the processor 550 can further be configured to update the configuration of the front edge 28 of the aligner 20 to enable concurrent use thereof with the orthodontic attachment 304.

Figure 14A:
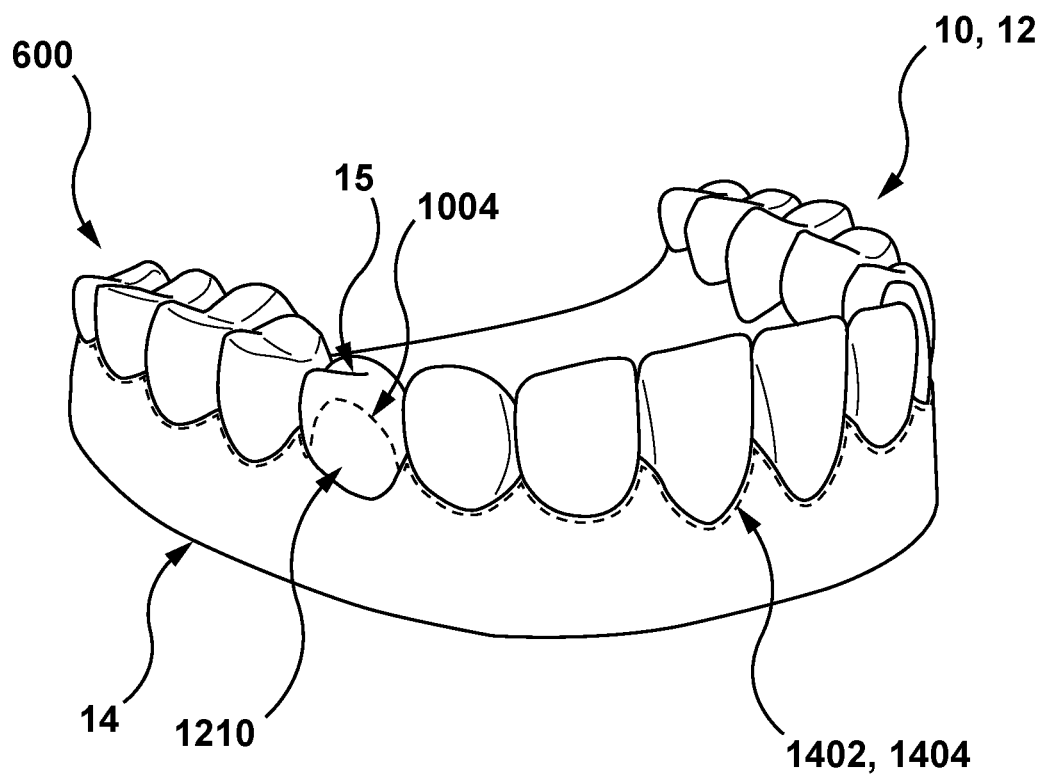
FIG. 14A depicts a schematic diagram of a cut line defining an updated profile of an open edge of the orthodontic appliance of FIGS. 2A and 2B, by the processor of FIG. 5, in the 3D digital model of the lower arch form of FIG. 6, based on the data of the positioning space of FIGS. 12A, 12B, 13A, and 13B, allowing accommodating the orthodontic attachment 304, in accordance with certain non-limiting embodiments of the present technology.

With reference to FIG. 14A, there is schematically depicted a cut line 1402 for the aligner 20 determined, by the processor, in the arch form 3D digital model 700, based on the data of the positioning space 1210 for accommodating the orthodontic attachment 304, in accordance with certain non-limiting embodiments of the present technology.

In some non-limiting embodiments of the present technology, the processor 550 can be configured to determine the cut line 1402 as a plurality of vertices 1404 following along the respective tooth-gingiva segmentation contours associated with each one of the lower teeth 12. To that end, for example, the processor 550 can be configured to apply one of the approaches described in a co-owned U.S. Pat. No. 11,058,515-B1, issued on Jul. 13, 2021, and entitled "SYSTEMS AND METHODS FOR FORMING DENTAL APPLIANCES", the content of which is incorporated herein by reference in its entirety.

However, along the given lower tooth 15, to which the orthodontic attachment 304 is to be attached, the processor 550 can be configured to determine the cut line 1402 as following a contour of the positioning space 1210 determined above, thereby defining the configuration of the cut-out in the aligner 20.

Further, in some non-limiting embodiments of the present technology, the processor 550 can be configured to cause display of the cut line 1402 within the arch form 3D digital model 600, such as on the screen 422 of the system 400 for presentation thereof, for example, to the dental practitioner involved in the development of the orthodontic treatment for the subject. Additionally, in some non-limiting embodiments of the present technology, the processor 550 can be configured to receive inputs from the dental practitioner for modifying the cut line 1402 based on their experience and expertise.

Also, in some non-limiting embodiments of the present technology, the processor 550 can be configured to store data indicative of the cut line 1402, such as coordinates of each one of the plurality of vertices 1404 thereof within the arch form 3D digital model 600, in the solid-state drive 560 of the system 400. Further, the processor 550 can be configured to use the data indicative of the cut line 1402 for producing the respective configuration of the aligner 20.

More specifically, as mentioned above, in some non-limiting embodiments of the present technology, the processor 550 may be configured to use the arch form 3D digital model 600 as a mold for producing the unfinished aligner using the thermoforming process. Further, the processor 550 can be configured to cause the marking subsystem 440 of the system 400 to apply each one of the plurality of vertices 1404 defining the cut line 1402 onto the unfinished aligner, as mentioned above. Further, the processor 550 may be configured to cause the forming subsystem 450 to detect, by the camera device 452, the cut line 1402 on the unfinished aligner and cut, by the cutting device 454, therealong, thereby producing the aligner 20 for use by the subject in the course of the orthodontic treatment. The aligner 20 so produced, when applied to the lower teeth 12, would have an updated profile of the front edge 28 configured for accommodating the orthodontic attachment 304 on the surface of the given lower tooth 15.

Figure 14B:
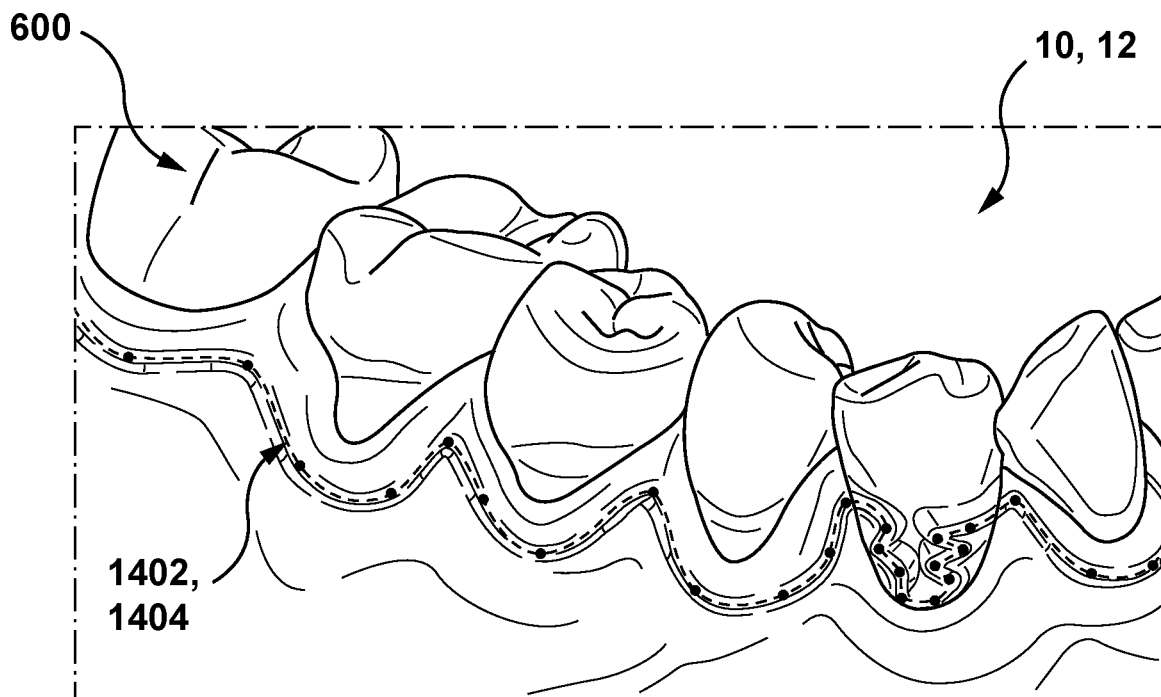
FIG. 14B depicts a schematic diagram of the cut line of FIG. 14A being embossed in a body of the 3D digital model of the lower arch form of FIG. 6, which can be used as a mold for producing the orthodontic appliance of FIGS. 2A and 2B, in accordance with certain non-limiting embodiments of the present technology.

However, in other non-limiting embodiments of the present technology, the aligner 20 can be formed from the unfinished aligner (not depicted) by manual cutting, which can be performed, for example, by an operator. To that end, in some non-limiting embodiments of the present technology, the processor 550 can be configured to emboss the cut line 1402 in a body of the arch form 3D digital model 600 such that the cut line 1402 is prominent along the surface of the arch form 3D digital model 600, as schematically depicted in FIG. 14B, for example. As it can be appreciated, once the unfinished aligner has been produced using such as a configuration of the mold, the position of the cutting line 1402 therealong can be determined, which may aid the operator in applying a cutting tool to the unfinished aligner for forming the aligner 20. By way of example, the cutting tool can include at least one of a mechanical cutting device (such as that having a blade with a rotary or linear cutting action, for example), a laser cutting device, or a water-jet based cutting device It should be noted that how a height of embossment of the cutting line 1402 is selected is not limited and, in some non-limiting embodiments of the present technology, can be predetermined, such as 2 mm, as an example. However, in other non-limiting embodiments of the present technology, an indication of a desired height of the embossment can be received, by the processor 550, from the operator.

In yet other non-limiting embodiments of the present technology, the processor 550 may be configured to use the arch form 3D digital model 600 with the cut line 1402 applied thereon to generate an aligner 3D digital model. Further, the processor 550 can be configured to cause production of the respective configuration of the aligner 20 by means of the 3D printing techniques according to the so generated aligner 3D digital model.

Method

Figure 15:
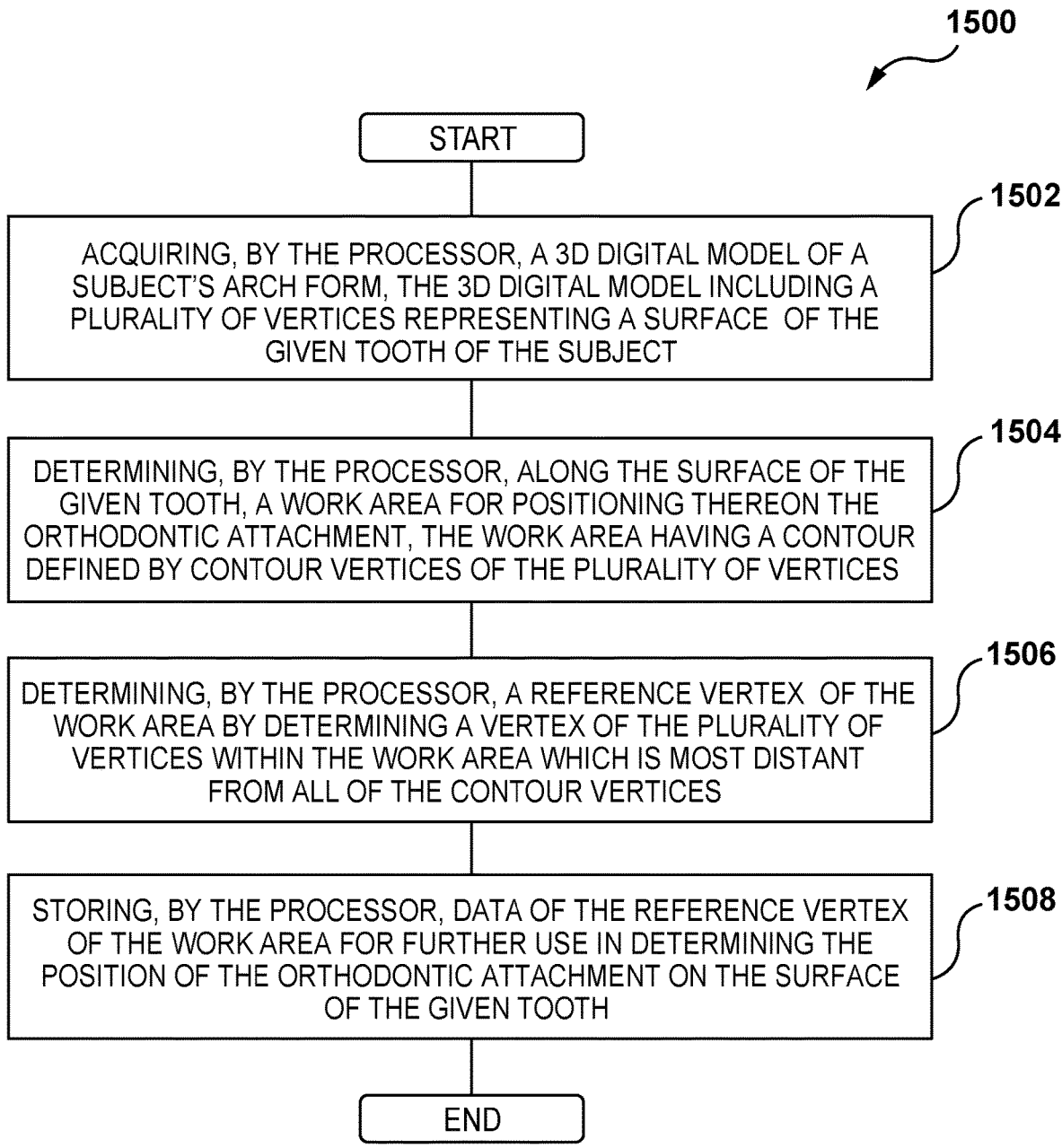
FIG. 15 depicts a flowchart diagram of a method for determining a positioning of the orthodontic attachment of FIG. 3B on the surface of the given tooth, in accordance with certain non-limiting embodiments of the present technology.

Given the architecture and the examples provided hereinabove, it is possible to execute a method for determining a position for an orthodontic attachment on a surface of the subject's tooth, such as a position for the orthodontic attachment 304 on the surface of the given lower tooth 15, as described above. With reference now to FIG. 15, there is depicted a flowchart of a method 1500, according to certain non-limiting embodiments of the present technology. The method 1500 may be executed by the processor 550 of the system 400.

Step 1502: Acquiring, by the Processor, a 3D Digital Model of a Subject's Arch Form, the 3D Digital Model Including a Plurality of Vertices Representing a Surface of the Given Tooth of the Subject The method 1500 commences at step 1502 with the processor 550 being configured to receive a 3D digital model of a subject's arch form, such as the arch form 3D digital model 600 of the lower arch form 10 of the subject, as described above with reference to FIG. 6.

Further, as further mentioned above, in some non-limiting embodiments of the present technology, the processor 550 can be configured to generate, based on the arch form 3D digital model 600, the tooth 3D digital model 700 of the given lower tooth 15, as an example.

The method 1500 hence advances to step 1504.

Step 1504: Determining, by the Processor, Along the Surface of the Given Tooth, a Work Area for Positioning Thereon the Orthodontic Attachment, the Work Area Having a Contour Defined by Contour Vertices of the Plurality of Vertices At step 1504, according to certain non-limiting embodiments of the present technology, the processor 550 can be configured to determine, using the tooth 3D digital model 700, the work area 910 on the surface of the given lower tooth 15 for positioning thereon the orthodontic attachment 304.

In some non-limiting embodiments of the present technology, the processor 550 can be configured to determine the work area by identifying, on the surface of the given lower tooth 15, an area of certain curvature—as described in greater detail above with reference to FIGS. 8, 9A, and 9B.

The method 1500 hence proceeds to step 1506.

Step 1506: Determining, by the Processor, a Reference Vertex of the Work Area by Determining a Vertex of the Plurality of Vertices within the Work Area which is Most Distant from all of the Contour Vertices Further, according to certain non-limiting embodiments of the present technology, the processor 550 can be configured to determine, within the work area 910, the positioning space 1210 corresponding to the geometry of the base portion 306 of the orthodontic attachment 304. To that end, as described above with reference to FIG. 9B, in some non-limiting embodiments of the present technology, the processor 550 can be configured to determine the first and second vertical boundaries for the positioning space 1210 within the work area 910.

According to certain non-limiting embodiments of the present technology, to determine the first vertical boundary, the processor 550 can be configured to determine, within the work area 910, the reference vertex 915. It is not limited how the processor 550 can be configured to determine the reference vertex 915. For example, the processor 550 can be configured to determine the reference vertex 915 as being a center of the work area 910.

However, in other non-limiting embodiments of the present technology, to determine the reference vertex 915, the processor 550 can be configured to: (i) identify the plurality of contour vertices 912 defining the contour of the work area 910; and (ii) determine the reference vertex 915 as being a vertex of the work area 910 that is most distant from all of the plurality of contour vertices 912. In some non-limiting embodiments of the present technology, the processor 550 can be configured to determine such a vertex by determining a vertex of the work area 910 from which a summation of all distance values therefrom to each one of the plurality of contour vertices 912, such as a given distance value 916, is maximum. To that end, the processor 550 can be configured to apply a Dijkstra algorithm, as an example.

The method 1500 hence advances to step 1508.

Step 1508: Storing, by the Processor, Data of the Reference Vertex of the Work Area for Further Use in Determining the Position of the Orthodontic Attachment on the Surface of the Given Tooth Further, at step 1508, according to certain non-limiting embodiments of the present technology, the processor 550 can be configured to store the data of the reference vertex 915, such as in the solid-state drive 560, for further use in determining the positioning space 1210 for the orthodontic attachment 304.

In alternative non-limiting embodiments of the present technology, the processor 550 can be configured to use the reference vertex 915 for determining the positioning space 1210 without storing it first. More specifically, as mentioned above, the processor 550 can be configured to determine the second vertical boundary within the work area 910 for the positioning space 1210.

In some non-limiting embodiments of the present technology, the processor 550 can be configured to determine the second vertical boundary for the positioning space 1210 as corresponding to the tooth-gingiva segmentation loop 602 representative of the boundary between the given lower tooth 15 and the lower gingiva 14. More specifically, the processor 550 can be configured to identify, on the tooth-gingiva segmentation loop 602, the plurality of additional reference vertices 1006, as described above with reference to FIGS. 10A and 10B, as being representative of the second vertical boundary within the work area 910 for the positioning space 1210.

Further, according to certain non-limiting embodiments of the present technology, the processor 550 can be configured to: (1) receive data representative of the orthodontic attachment 304 including, for example, that of the shape and dimensions of the base portion 306 thereof, as described above; (2) retrieve, based on the data of the orthodontic attachment 304, for example, from the solid-state drive 560 of the computing environment 540, data representative of a respective pattern corresponding in shape to base portion 306 of the orthodontic attachment 304; and (3) fit the respective pattern on the surface of the tooth 3D digital model 700 between the first and second vertical boundaries determined.

For example, as described above with reference to FIG. 11, in some non-limiting embodiments of the present technology, the processor 550 can be configured to select, based on the data representative of the orthodontic attachment 304, the respective pattern from the plurality of patterns 1102—such as the given pattern 1104.

Further, to fit the given pattern 1104 between the first vertical boundary and the second vertical boundary on the work area 910, in some non-limiting embodiments of the present technology, the processor 550 can be configured to apply one or more transformations to the given pattern 1104, as described above with reference to FIGS. 12A and 12B.

However, in other non-limiting embodiments of the present technology, as described above with reference to FIGS. 13A and 13B, the processor 550 can be configured to shape the positioning space 1210 from the plurality of additional reference vertices 1006. To that end, the processor 550 can be configured to consider the plurality of additional reference vertices 1006 as defining segments of a continuous curve, such that a modification to any of the so defined segments, such as stretching, translation, or rotation, would not cause the curve to break. Further, the processor 550 can be configured to join the plurality of additional reference vertices 1006, so re-arranged within the work area 910, as described above.

Further, in accordance with certain non-limiting embodiments of the present technology, based on data of the positioning space 1210, the processor 550 can be configured to determine a cut line, such as the cut line 1402 described above with reference to FIG. 14A, defining the updated configuration of the front edge 28 of the aligner 20.

Further, in some non-limiting embodiments of the present technology, the processor 550 can be configured to cause display of the cut line 1402 within the arch form 3D digital model 600, such as on the screen 422 of the system 400 for presentation thereof, for example, to the dental practitioner involved in the development of the orthodontic treatment for the subject. Additionally, in some non-limiting embodiments of the present technology, the processor 550 can be configured to receive inputs from the dental practitioner for modifying the cut line 1402 based on their experience and expertise.

Also, in some non-limiting embodiments of the present technology, the processor 550 can be configured to store data indicative of the cut line 1402, such as coordinates of each one of the plurality of vertices 1404 thereof within the arch form 3D digital model 600, in the solid-state drive 560 of the system 400. Further, the processor 550 can be configured to use the data indicative of the cut line 1402 for producing the respective configuration of the aligner 20 having the updated configuration of the front edge 28, as described above with reference to FIGS. 14A and 14B. This configuration of the front edge 28 of the aligner 20 can thus enable concurrent use thereof with the orthodontic attachment 304.

The method 1500 thus terminates.

Thus, certain non-limiting embodiments of the method 1500 allow determining the positioning space 1210 for the orthodontic attachment 304 that would allow a more accurate application of the elastic forces to the lower teeth 12 via the orthodontic elastic 302 received on the orthodontic attachment 304, as well as improved wear comfort of the aligner 20 during its concurrent use with the orthodontic attachment 304.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to providing examples of implementations of the present technology rather than being limiting. The scope of the present technology is therefore intended to be limited solely by the scope of the appended claims.

The invention claimed is:

1. A method of determining a position of an orthodontic attachment on a surface of a given tooth of a subject, the method being executable by a processor, the method comprising:
    acquiring, by the processor, a 3D digital model of a subject's arch form, the 3D digital model including a plurality of vertices representing a surface of the given tooth of the subject;
    determining, by the processor, along the surface of the given tooth, a work area for positioning thereon the orthodontic attachment, the work area having a contour defined by contour vertices of the plurality of vertices;
    determining, by the processor, a reference vertex of the work area by determining a vertex of the plurality of vertices within the work area which is most distant from all of the contour vertices,
        the reference vertex being representative of a boundary of a space within the work area for positioning therein the orthodontic attachment; and
    storing, by the processor, data of the reference vertex of the work area for further use in determining the position of the orthodontic attachment on the surface of the given tooth.

2. The method of claim 1, wherein:
    the plurality of vertices of the 3D digital model of the subject's arch form further includes vertices representing surfaces of a plurality of the subject's teeth, including the given tooth, and wherein:

the determining the contour of the work area comprises:
  obtaining, by the processor, a jaw curve extending through each one of the plurality of subject's teeth along the subject's arch form;
  determining, by the processor, a reference plane extending through the given tooth, in a buccolabial direction thereof, perpendicularly to the jaw curve;
  for a given vertex representative of the surface of the given tooth, determining, by the processor, a respective angular difference between a normal vector to the surface at the given vertex and the reference plane;
  in response to the respective angular difference being greater than a predetermined angular threshold value, removing, by the processor, the given vertex from further consideration; and
  in response to the respective angular difference being lower than or equal to the predetermined angular threshold value, determining, by the processor, the given vertex as being representative of the work area of the surface of the given tooth for positioning thereon the orthodontic attachment.

3. The method of claim 2, further comprising determining the jaw curve as a curve extending through respective centers of each one of the plurality of the subject's teeth.

4. The method of claim 1, wherein the determining the vertex of the plurality of vertices within the work area which is most distant from all of the contour vertices comprises determining a vertex from which a summation of distance values to each one of the contour vertices is maximum.

5. The method of claim 4, wherein the determining the vertex from which the summation of the distance values to each one of the contour vertices is maximum comprises applying a Dijkstra algorithm.

6. The method of claim 1, further comprising determining, by the processor, the reference vertex of the work area as corresponding to a vertical boundary of the space within the work area, towards a crown of the given tooth, for positioning thereon the orthodontic attachment.

7. The method of claim 6, further comprising:
  retrieving, from a memory communicatively coupled with the processor, a respective pattern representative of a shape of the space within the work area associated with the given tooth for positioning thereon the orthodontic attachment;
  fitting the respective pattern within the work area such that at least one first peak point of the respective pattern positioned towards the crown of the given tooth matches the reference vertex of the work area; and
  adding, by the processor, to the 3D digital model of the subject's arch form, an indication of the respective pattern fitted within the work area associated with the given tooth for further use in producing an orthodontic appliance.

8. The method of claim 7, wherein the plurality of vertices of the 3D digital model further includes vertices representing a gingiva of the subject, and the method further comprises:
  obtaining, by the processor, a segmentation contour representative of a boundary between the given tooth and the gingiva;
  identifying, on the segmentation contour along the work area, based on a predetermined rule, additional reference vertices for positioning the orthodontic attachment; and wherein:
  the fitting further comprises fitting the respective pattern within the work area such that at least one second peak point of the respective pattern, oppositely facing the at least one first peak point, matches a respective one of the additional reference vertices.

9. The method of claim 8, wherein the additional reference vertices are distributed uniformly along the segmentation contour.

10. The method of claim 9, further comprising causing manufacture of the orthodontic appliance based at least on the determined profile of the free end thereof.

11. The method of claim 8, further comprising determining the segmentation contour.

12. The method of claim 11, wherein the orthodontic attachment is an elastic retaining member.

13. The method of claim 11, wherein the orthodontic appliance is an orthodontic aligner.

14. The method of claim 8, further comprising determining, based at least on a configuration of the cut-out, a profile of a free end of the orthodontic appliance configured for accommodating therein the orthodontic attachment.

15. The method of claim 7, wherein the fitting comprises scaling the respective pattern within the work area in at least one direction thereof.

16. The method of claim 7, wherein:
  the orthodontic attachment is to be applied to the given tooth concurrently with the orthodontic appliance; and
  a contour of the space within the work area associated with the given tooth defines a cut-out in the orthodontic appliance for accommodating therein the orthodontic attachment when applied to the subject's arch form.

17. A system for determining a position of an orthodontic attachment on a surface of a given tooth of a subject, the system including:
  a processor and
  a non-transitory computer-readable memory storing instructions, and
  the processor, upon executing the instructions, being configured to:
    acquire a 3D digital model of a subject's arch form, the 3D digital model including a plurality of vertices representing a surface, at least, of the given tooth of the subject;
    determine, along the surface of the given tooth, a work area for positioning thereon the orthodontic attachment, the work area having a contour defined by contour vertices of the plurality of vertices;
    determine a reference vertex of the work area by determining a vertex of the plurality of vertices within the work area which is most distant from all of the contour vertices,
      the reference vertex being representative of a boundary of a space within the work area for positioning therein the orthodontic attachment; and
    store data of the reference vertex of the work area for further use in positioning the orthodontic attachment on the surface of the given tooth.

18. The system of claim 17, wherein:
  the plurality of vertices of the 3D digital model of the subject's arch form further includes vertices representing surfaces of a plurality of a subject's teeth, including the given tooth, and wherein to determine the contour of the work area, the processor is further configured to:
    obtain a jaw curve extending through each one of the plurality of the subject's teeth along the subject's arch form;

determine a reference plane extending through the given tooth, in a buccolabial direction thereof, perpendicularly to the jaw curve;

for a given vertex representative of the surface of the given tooth, determine a respective angular difference between a normal vector to the surface at the given vertex and the reference plane;

in response to the respective angular difference being greater than a predetermined angular threshold value, remove the given vertex from further consideration; and in response to the respective angular difference being lower than or equal to the predetermined angular threshold value, determine the given vertex as being representative of the work area of the surface of the given tooth for positioning there on the orthodontic attachment.

19. The system of claim 17, wherein to determine the vertex of the plurality of vertices within the work area which is most distant from all of the contour vertices, the processor is configured to determine a vertex from which a summation of distance values to each one of the contour vertices is maximum.

20. The system of claim 17, wherein the processor is further configured to:

determine the reference vertex of the work area as corresponding to a vertical boundary of a space within the work area, towards a crown of the given tooth, for positioning thereon the orthodontic attachment;

retrieve, from the non-transitory computer-readable memory, a respective pattern representative of a shape of the space within the work area associated with the given tooth for positioning thereon the orthodontic attachment;

fir the respective pattern within the work area such that at least one first peak point of the respective pattern positioned towards the crown of the given tooth matches the reference vertex of the work area; and add, to the 3D digital model of the subject's arch form, an indication of the respective pattern fitted within the work area associated with the given tooth for further use in producing an orthodontic appliance.

\* \* \* \* \*